US012758566B2

(12) United States Patent
Docherty et al.

(10) Patent No.: US 12,758,566 B2
(45) **Date of Patent: *Oct. 13, 2026**

(54) COMPOSITIONS AND METHODS FOR TREATING DIABETES

(71) Applicant: POVIVA CORP, Carson City, NV (US)

(72) Inventors: John Docherty, Port Perry (CA); Christopher Andrew Bunka, Kelowna (CA)

(73) Assignee: POVIVA CORP, Carson City, NV (US)

( * ) Notice: Subject to any disclaimer, the term of this patent is extended or adjusted under 35 U.S.C. 154(b) by 282 days.

This patent is subject to a terminal disclaimer.

(21) Appl. No.: 18/747,862

(22) Filed: Jun. 19, 2024

(65) Prior Publication Data

US 2025/0387416 A1 Dec. 25, 2025

(51) Int. Cl.

| | |
|---|---|
| ***A61K 31/00*** | (2006.01) |
| ***A61K 47/02*** | (2006.01) |
| ***A61K 47/28*** | (2006.01) |
| ***A61K 47/44*** | (2017.01) |
| ***A61P 3/10*** | (2006.01) |

(52) U.S. Cl.
CPC ............ *A61K 31/658* (2023.05); *A61K 47/02* (2013.01); *A61K 47/28* (2013.01); *A61K 47/44* (2013.01); *A61P 3/10* (2018.01)

(58) Field of Classification Search
CPC ...... A61K 31/658; A61K 47/02; A61K 47/28; A61K 47/44; A61P 3/10
See application file for complete search history.

(56) References Cited

U.S. PATENT DOCUMENTS

| | | | | |
|---|---|---|---|---|
| 11,666,544 B1 * | 6/2023 | Docherty ............. | A61K 31/658 424/725 |
| 11,931,369 B1 | 3/2024 | Docherty et al. | |
| 11,944,635 B1 | 4/2024 | Docherty et al. | |
| 11,986,485 B1 * | 5/2024 | Docherty ............... | A61K 31/05 |
| 12,023,346 B1 | 7/2024 | Docherty et al. | |
| 2022/0133683 A1 * | 5/2022 | Crisler ................. | A61K 31/658 514/456 |

OTHER PUBLICATIONS

Zhang et al. (Exploration 2023, 3, 20230047. doi.org/10.1002/EXP.20230047) (Year: 2023).*
U.S. Appl. No. 18/225,270, Compositions and Methods for Treating Epilepsy, filed Jul. 24, 2023.
U.S. Appl. No. 18/417,226, Compositions and Methods for Treating Epilepsy, filed Jan. 19, 2024.
U.S. Appl. No. 18/417,252, Compositions and Methods for Treating Epilepsy, filed Jan. 19, 2024.
U.S. Appl. No. 18/442,061, Compositions and Methods for Treating Epilepsy, filed Feb. 14, 2024.

* cited by examiner

*Primary Examiner* — Brandon J Fetterolf
(74) *Attorney, Agent, or Firm* — FisherBroyles LLP; Anthony J DoVale; Richard Echler

(57) ABSTRACT

Disclosed herein are compositions and methods for treating diabetes. The disclosed compositions are also effective for reducing body weight and improving triglyceride and cholesterol levels.

30 Claims, 5 Drawing Sheets

COMPOSITIONS AND METHODS FOR TREATING DIABETES

FIELD

Disclosed herein are compositions and methods for treating diabetes. The disclosed compositions are also effective for reducing body weight and improving triglyceride and cholesterol levels.

DETAILED DESCRIPTION OF THE DISCLOSURE

Figure 1:
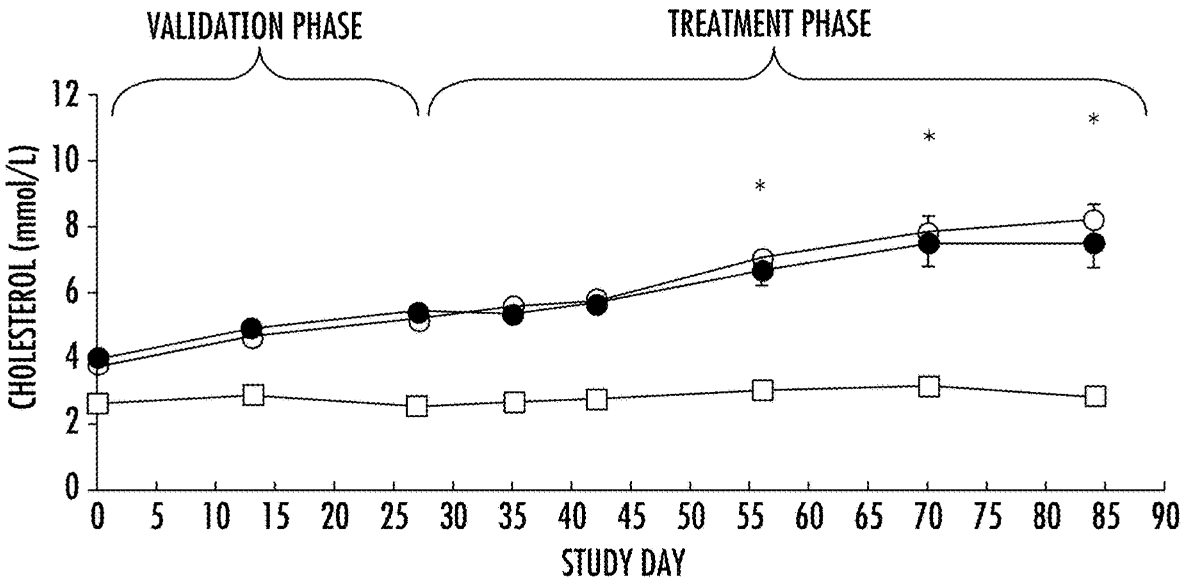
FIG. 1 shows the cholesterol levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated.

The materials, compounds, compositions, articles, and methods described herein may be understood more readily by reference to the following detailed description of specific aspects of the disclosed subject matter and the Examples included therein.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the disclosed methods or compositions can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

As used herein, the term "subject" refers to a human or an animal that would benefit from being administered with the disclosed compositions described in the present application, such as those suffering from, without limitation one or more forms of epilepsy.

As used herein, the terms "treat," "treating," "treatment," and the like refer to reducing or ameliorating a disorder and/or symptoms associated therewith. It will be appreciated that, although not precluded, treating epilepsy does not require that the epilepsy, condition or symptoms associated epilepsy be completely eliminated.

As used herein, the terms "prevent," "preventing," "prevention," "prophylactic treatment" and the like are encompassed within the term "treating," and refer to reducing the probability of developing a disorder or condition in a subject, who does not have, but is at risk of or susceptible to developing a disorder or condition.

As used herein, "pharmaceutically acceptable" means physiologically tolerable, for either human or veterinary applications. In addition, "pharmaceutically acceptable" is meant a material that is not biologically or otherwise undesirable, i.e., the material may be administered to a subject without causing any undesirable biological effects or interacting in a deleterious manner with any of the other components of the pharmaceutical composition in which it is contained. Essentially, the pharmaceutically acceptable material is nontoxic to the recipient. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990.

The term "pharmaceutical composition" is defined herein as a composition which is approved by a regulatory body, for example, the Food and Drug Administration (FDA), European Medicines Agency (EMA), Japanese Pharmaceutical and Food Safety Bureau (PFSB), and the like.

The term "over-the-counter" or "OTC" or "non-pharmaceutical" is defined herein as disclosed compositions that can be bought and sold without a prescription.

The feature or features of one embodiment may be applied to other embodiments, even though not described or illustrated, unless expressly prohibited by this disclosure or the nature of the embodiments.

The term "high oleic acid sunflower oil" means sunflower oil that contains a greater than average amount of oleic acid fatty acids which make up the triglycerides of the sunflower oil. For example, sunflower oil comprising at a minimum 80% of the fatty acids which comprise the triglycerides are oleic acids. This higher level of oleic acid can be achieved by selected extraction of the oil, post processing combining with high oleic acid fractions of sunflower oil, genetic modification, and the like.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and describe the methods and/or materials in connection with which the publications are cited.

Cannabidiol

Cannabidiol (CBD) is a non-psychoactive component of *Cannabis sativa*. It is one of the main components that make up extracts of *cannabis* plants. Although CBD oil is a term of commerce, the amount of cannabidiol present in the CBD oils varies depending upon the method of extraction.

In general, CBD oil (the extract of *Cannabis sativa*) is defined in part by the following which are currently recognized guidelines for the contents and quality of CBD oil:

Full-spectrum CBD products generally contain the full range of terpenes and cannabinoids present in the source plant (including any trace amounts of THC), which boosts the so called entourage effect when consumed. This is the crudest form of CBD oil.

Broad-spectrum CBD products generally contain some other cannabinoids beyond CBD and all or most of the terpenes present in the source plant, but most or all of the THC has been stripped away. Typically the amount of THC is less than about 0.5%, however, any extracted cannabidiol in the form of CBD and/or hemp oil contains less than about 0.15% by weight of THC. This form is typically used in over-the-counter applications and is frequently known as CBD "tincture." This tincture is typically marketed with an eye dropper for application under the tongue.

Isolate is pure CBD with virtually all other compounds removed. Isolate CBD products have their own unique benefits, but they do not offer the same entourage effect that full- or broad-spectrum CBD products can. This is nearly chemically pure cannabidiol (generally at least about 98%-99% cannabidiol) in the form of a powder rather than liquid oil, which is suitable for many applications including "proof of concept" testing in a pre-pharmaceutical setting as well as in pharmaceutical preparations when manufactured according to pharmaceutical standards. For the purposes of the present disclosure cannabidiol refers to the isolate having greater than about 98% by weight of 2-[(1R,6R)-6-Isopropenyl-3-methylcyclohex-2-en-1-yl]-5-pentylbenzene-1,3-diol. In addition, the cannabidiol used to formulate the disclosed pharmaceutical compositions comprise less than about 0.15% of $\Delta^9$-tetrahydrocannabinol (THC).

The terms "Full-spectrum CBD" is defined as above. The term "CBD" or "CBD oil" is the "Broad-spectrum CBD" as defined above. Those skilled in the art of formulating cannabidiol recognize that pharmaceutical compositions require cannabidiol be present in the pure form. Therefore, CBD, CBD oil, etc. would only be suitable for non-prescription or over-the-counter formulations.

According to the present disclosure the base compositions can comprise CBD oil. What is meant herein by the term "CBD oil" is the cannabidiol-containing extract from the hemp plant *Cannabis sativa*. The CBD oil useful for preparing the disclosed compositions can be extracts which are crude extracts containing less than about 80% by weight of cannabidiol. As used herein CBD oil comprising less than about 80% by weight of cannabidiol is referred to a "crude CBD oil." When using lower percentage extracts the formulator will necessarily adjust the amount of CBD oil present in the disclosed compositions to ensure adequate delivery of the desired amount of cannabidiol.

In one embodiment, the compositions comprise a "hemp distillate" comprising from about 80% to about 92% by weight of cannabidiol. In a still further embodiment isolated, pure cannabidiol can be used in the present compositions. When the hemp distillate comprising from 80% to about 92% by weight cannabidiol is used, the term "CBD oil" applies. In some descriptions of the "CBD oil" this ingredient can be referred to as a "CBD resin." All CBD oil compositions contain CBD oil having less than 0.3% by weight of tetrahydrocannabinol (THC).

Compositions

The various aspects of the disclosed compositions and methods relate to compositions comprising cannabidiol. Cannabidiol has the chemical name 2-[(1R,6R)-6-Isopropenyl-3-methylcyclohex-2-en-1-yl]-5-pentylbenzene-1,3-diol. The disclosed compositions of these aspects comprise CBD oil containing from about 80% to about 92% by weight of cannabidiol. In addition, CBD oil extracts containing about 98% by weight or greater cannabidiol comprises less than about 0.15% THC.

The disclosed compositions are free flowing solids that can be incorporated into any acceptable form, for example, capsule, pill, lozenge, and the like Aspects of the Disclosed Compositions One aspect the disclosed compositions comprise:

a) from about 0.5% to about 10% by weight of CBD oil wherein the CBD oil contains from about 86% to about 92% by weight of cannabidiol;
b) from about 1% to about 20% by weight of high oleic acid sunflower oil;
c) from about 10% to about 25% by weight of sodium bicarbonate;
d) from about 25% to about 35% by weight of one or more bile salt extracts; and
e) from about 35% to about 55% by weight of one or more carriers.

In one embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts; and
e) from about 40% to about 50% by weight of one or more carriers chosen from gum Arabic, tapioca starch, tapioca flour, silicon dioxide, mannitol, colloidal silicon dioxide, and mixture thereof.

In one iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts; and
e) from about 40% to about 50% by weight of gum Arabic.

In another iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of gum Arabic.

In a further iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts; and
e) from about 40% to about 50% by weight of one or more carriers chosen from tapioca starch, tapioca flour, and mixture thereof.

In a still further iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from tapioca starch, tapioca flour, and mixture thereof.

In a still further iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts; and
e) from about 40% to about 50% by weight of one or more carriers chosen from silicon dioxide, mannitol, colloidal silicon dioxide, and mixture thereof.

In a yet still further iteration of this embodiment of this aspect, the compositions comprise:

a) from about 1% to about 5% by weight of CBD oil wherein the CBD oil contains from about 86% to about 92% by weight of cannabidiol;
b) from about 4% to about 8% by weight of high oleic acid sunflower oil;
c) from about 12% to about 18% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from silicon dioxide, mannitol, colloidal silicon dioxide, and mixture thereof.

In another aspect the disclosed compositions comprise:

a) from about 1% to about 10% by weight of CBD oil wherein the CBD oil contains from about 86% to about 92% by weight of cannabidiol;
b) from about 5% to about 15% by weight of high oleic acid sunflower oil;
c) from about 10% to about 25% by weight of sodium bicarbonate;
d) from about 25% to about 35% by weight of one or more bile salt extracts; and
e) from about 35% to about 55% by weight of one or more carriers.

In one embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from gum Arabic, tapioca starch, tapioca flour, silicon dioxide, mannitol, colloidal silicon dioxide, and mixture thereof.

In one iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of gum Arabic.

In another iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of gum Arabic.

In a further iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from tapioca starch, tapioca flour, and mixture thereof.

In a still further iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from tapioca starch, tapioca flour, and mixture thereof.

In a still further iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from silicon dioxide, mannitol, colloidal silicon dioxide, and mixture thereof.

In a yet still further iteration of this embodiment of this aspect, the compositions comprise:

a) from about 1% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from silicon dioxide, mannitol, colloidal silicon dioxide, and mixture thereof.

In a further aspect the disclosed compositions comprise:

a) from about 2% to about 4% by weight of CBD oil wherein the CBD oil contains from about 86% to about 92% by weight of cannabidiol;
b) from about 5% to about 15% by weight of high oleic acid sunflower oil;
c) from about 10% to about 25% by weight of sodium bicarbonate;
d) from about 25% to about 35% by weight of one or more bile salt extracts; and
e) from about 35% to about 55% by weight of one or more carriers.

In one embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from gum Arabic, tapioca starch, tapioca flour, silicon dioxide, mannitol, colloidal silicon dioxide, and mixture thereof.

In one iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of gum Arabic.

In another iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of gum Arabic.

In a further iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from tapioca starch, tapioca flour, and mixture thereof.

In a still further iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from tapioca starch, tapioca flour, and mixture thereof.

In a still further iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts; and
e) from about 40% to about 50% by weight of one or more carriers chosen from silicon dioxide, mannitol, colloidal silicon dioxide, and mixture thereof.

In a yet still further iteration of this embodiment of this aspect, the compositions comprise:

a) from about 2% to about 4% by weight of CBD oil wherein the CBD oil contains from about 86% to about 92% by weight of cannabidiol;
b) from about 5% to about 7% by weight of high oleic acid sunflower oil;
c) from about 13% to about 17% by weight of sodium bicarbonate;
d) from about 28% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 40% to about 50% by weight of one or more carriers chosen from silicon dioxide, mannitol, colloidal silicon dioxide, and mixture thereof.

In a further aspect the disclosed compositions comprise:

a) from about 2.5% to about 4% by weight of CBD oil wherein the CBD oil contains from about 86% to about 92% by weight of cannabidiol;
b) from about 5% to about 15% by weight of high oleic acid sunflower oil;
c) from about 10% to about 25% by weight of sodium bicarbonate;
d) from about 28% to about 31% by weight of one or more bile salt extracts; and
e) from about 42% to about 48% by weight of one or more carriers.

In one embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts; and
e) from about 42% to about 48% by weight of one or more carriers chosen from gum Arabic, tapioca starch, tapioca flour, silicon dioxide, mannitol, colloidal silicon dioxide, and mixture thereof.

In one iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts; and
e) from about 42% to about 48% by weight of gum Arabic.

In another iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts wherein the bile salts are an extract containing from about 45% to about 55% by weight of cholic acid, deoxycholic acid, taurocholate, glycocholic acid, and mixtures thereof; and
e) from about 42% to about 48% by weight of gum Arabic.

In a further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 321% by weight of one or more bile salt extracts; and
e) from about 42% to about 48% by weight of one or more carriers chosen from tapioca starch, tapioca flour, and mixture thereof.

In a still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts wherein the bile salts are an extract containing from about 45% to about 55% by weight of cholic acid, deoxycholic acid, taurocholate, glycocholic acid, and mixtures thereof; and
e) from about 42% to about 48% by weight of one or more carriers chosen from tapioca starch, tapioca flour, and mixture thereof.

In a still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts; and
e) from about 42% to about 48% by weight of one or more carriers chosen from silicon dioxide, mannitol, colloidal silicon dioxide, and mixture thereof.

In a yet still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 31% by weight of one or more bile salt extracts wherein the bile salts are an extract containing from about 45% to about 55% by weight of cholic acid, deoxycholic acid, taurocholate, glycocholic acid, and mixtures thereof; and
e) from about 42% to about 48% by weight of one or more carriers chosen from silicon dioxide, mannitol, colloidal silicon dioxide, and mixture thereof.

In a further aspect the disclosed compositions comprise:

a) from about 2.5% to about 4% by weight of CBD oil wherein the CBD oil contains from about 86% to about 92% by weight of cannabidiol;
b) from about 5% to about 15% by weight of high oleic acid sunflower oil;
c) from about 10% to about 25% by weight of sodium bicarbonate;
d) from about 29% to about 32% by weight of one or more bile salt extracts; and
e) from about 43% to about 47% by weight of one or more carriers.

In one embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts; and
e) from about 43% to about 47% by weight of one or more carriers chosen from gum Arabic, tapioca starch, tapioca flour, silicon dioxide, mannitol, colloidal silicon dioxide, and mixture thereof.

In one iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts; and
e) from about 43% to about 47% by weight of gum Arabic.

In another iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts wherein the bile salts are an extract containing from about 45% to about 55% by weight of cholic acid, deoxycholic acid, taurocholate, glycholic acid, and mixtures thereof; and e) from about 43% to about 47% by weight of gum Arabic.

In a further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 28% to about 321% by weight of one or more bile salt extracts; and
e) from about 43% to about 47% by weight of one or more carriers chosen from tapioca starch, tapioca flour, and mixture thereof.

In a still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 43% to about 47% by weight of one or more carriers chosen from tapioca starch, tapioca flour, and mixture thereof.

In a still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts; and
e) from about 43% to about 47% by weight of one or more carriers chosen from silicon dioxide, mannitol, colloidal silicon dioxide, and mixture thereof.

In a yet still further iteration of this embodiment of this aspect, the compositions comprise:

a) from about 2.5% to about 4% by weight of CBD oil wherein the CBD oil contains from about 86% to about 92% by weight of cannabidiol;
b) from about 5% to about 7% by weight of high oleic acid sunflower oil;
c) from about 14% to about 17% by weight of sodium bicarbonate;
d) from about 29% to about 32% by weight of one or more bile salt extracts wherein the bile salts are an extract containing from about 45% to about 55% by weight of cholic acid, deoxycholic acid, taurocholate, glycocholic acid, and mixtures thereof; and
e) from about 43% to about 47% by weight of one or more carriers chosen from silicon dioxide, mannitol, colloidal silicon dioxide, and mixture thereof.

In one non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;
d) about 30% by weight of one or more bile salt extracts; and
e) from about 45% to about 55% by weight of one or more carriers.

In another non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;
d) about 30% by weight of one or more bile salt extracts wherein the bile salts are an extract containing from about 45% to about 55% by weight of cholic acid, deoxycholic acid, taurocholate, glycocholic acid, and mixtures thereof; and
e) from about 45% to about 55% by weight of one or more carriers.

In a further non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;
d) about 30% by weight of one or more bile salt extracts; and
e) about 46% by weight of gum Arabic.

In a further non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;
d) about 30% by weight of one or more bile salts wherein the bile salts are an extract containing from about 45% to about 55% by weight of cholic acid, deoxycholic acid, taurocholate, glycocholic acid, and mixtures thereof; and
e) from about 45% to about 46% by weight of gum Arabic.

In a further non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;
d) about 30% by weight of one or more bile salt extracts; and
e) about 46% by weight of one or more carriers chosen from tapioca starch, tapioca flour, and mixture thereof.

In a further non-limiting example of the disclosed compositions, the compositions comprise:

a) about 3% by weight of CBD oil wherein the CBD oil contains from about 89% to about 91% by weight of cannabidiol;
b) about 6% by weight of high oleic acid sunflower oil;
c) about 15% by weight of sodium bicarbonate;

d) about 30% by weight of one or more bile salts wherein the bile salts are an extract containing from about 45% to about 55% by weight of cholic acid, deoxycholic acid, taurocholate, glycocholic acid, and mixtures thereof; and e) from about 45% to about 46% by weight of one or more carriers chosen from silicon dioxide, mannitol, colloidal silicon dioxide, and mixture thereof.

The disclosed compositions can comprise from about 0.5% to about 10% by weight of CBD oil wherein the CBD oil contains from about 86% to about 92% by weight of cannabidiol. The CBD oil that comprises the compositions disclosed herein can contain any amount of cannabidiol from about 86% to about 92% by weight, for example, 88%, 88.5%, 89%, 89.5%, 90%, 90.5%, 91%, 91.5%, 92%, or any other fractional amount thereof. Non-limiting examples of fractional amounts includes 88.75%, 90.64%, 91.26%, and the like.

In one aspect, the disclosed compositions can comprise from about 0.5% to about 10% by weight of CBD oil. In one embodiment, the disclosed compositions comprise from about 1% to about 5% by weight of CBD oil. In another embodiment, the disclosed compositions comprise from about 2% to about 5% by weight of CBD oil. In a further embodiment, the disclosed compositions comprise from about 1% to about 4% by weight of CBD oil. In a yet further embodiment, the disclosed compositions comprise from about 2% to about 4% by weight of CBD oil. In a still further embodiment, the disclosed compositions comprise from about 2.5% to about 4% by weight of CBD oil.

The disclosed compositions can comprise from about 0.5% to about 10% by weight of CBD oil wherein the CBD oil contains from about 86% to about 92% by weight of cannabidiol, for example, 0.5%, 0.55%, 0.6%, 0.65%, 0.7%, 0.75%, 0.8%, 0.85%, 0.9%, 0.95%, 1%, 1.1%, 1.15%, 1.2%, 1.25%, 1.3%, 1.35%, 1.4%, 1.45%, 1.5%, 1.55%, 1.6%, 1.65%, 1.7%, 1.75%, 1.8%, 1.85%, 1.9%, 1.95%, 2%, 2.1%, 2.15%, 2.2%, 2.25%, 2.3%, 2.35%, 2.4%, 2.45%, 2.5%, 2.55%, 2.6%, 2.65%, 2.7%, 2.75%, 2.8%, 2.85%, 2.9%, 2.95%, 3%, 3.1%, 3.15%, 3.2%, 3.25%, 3.3%, 3.35%, 3.4%, 3.45%, 3.5%, 3.55%, 3.6%, 3.65%, 3.7%, 3.75%, 3.8%, 3.85%, 3.9%, 3.95%, 4%, 4.1%, 4.15%, 4.2%, 4.25%, 4.3%, 4.35%, 4.4%, 4.45%, 4.5%, 4.55%, 4.6%, 4.65%, 4.7%, 4.75%, 4.8%, 4.85%, 4.9%, 4.95%, 5%, 5.1%, 5.15%, 5.2%, 5.25%, 5.3%, 5.35%, 5.4%, 5.45%, 5.5%, 5.55%, 5.6%, 5.65%, 5.7%, 5.75%, 5.8%, 5.85%, 5.9%, 5.95%, 6%, 6.1%, 6.15%, 6.2%, 6.25%, 6.3%, 6.35%, 6.4%, 6.45%, 6.5%, 6.55%, 6.6%, 6.65%, 6.7%, 6.75%, 6.8%, 6.85%, 6.9%, 6.95%, 7%, 7.1%, 7.15%, 7.2%, 7.25%, 7.3%, 7.35%, 7.4%, 7.45%, 7.5%, 7.55%, 7.6%, 7.65%, 7.7%, 7.75%, 7.8%, 7.85%, 7.9%, 7.95%, 8%, 8.1%, 8.15%, 8.2%, 8.25%, 8.3%, 8.35%, 8.4%, 8.45%, 8.5%, 8.55%, 8.6%, 8.65%, 8.7%, 8.75%, 8.8%, 8.85%, 8.9%, 8.95%, 9%, 9.1%, 9.15%, 9.2%, 9.25%, 9.3%, 9.35%, 9.4%, 9.45%, 9.5%, 9.55%, 9.6%, 9.65%, 9.7%, 9.75%, 9.8%, 9.85%, 9.9%, 9.95%, or 10% by weight of CBD oil.

In one aspect, the disclosed compositions can comprise from about 1% to about 20% by weight of high oleic acid sunflower oil. In one embodiment, the disclosed compositions comprise from about 4% to about 8% by weight of high oleic acid sunflower oil. In another embodiment, the disclosed compositions comprise from about 4% to about 8% by weight of high oleic acid sunflower oil. In a further embodiment, the disclosed compositions comprise from about 5% to about 8% by weight of high oleic acid sunflower oil. In yet further embodiment, the disclosed compositions comprise from about 5% to about 7% by weight of high oleic acid sunflower oil. In a still yet further embodiment, the disclosed compositions comprise from about 5% to about 15% by weight of high oleic acid sunflower oil. In another still yet further embodiment, the disclosed compositions comprise from about 1% to about 10% by weight of high oleic acid sunflower oil. The disclosed compositions can comprise from about 1% to about 20% by weight of high oleic acid sunflower oil, for example, 1%, 2%, 3%, 4%, 5%, 6%, 7%, 8%, 9%, 10%, 11%, 12%, 13%, 14%, 15%, 16%, 17%, 18%, 19%, or 20%. The ratio of CBD oil containing from about 86% to about 92% by weight of cannabidiol to high oleic acid sunflower oil can be 1:1, 1:1.1, 1:1.2, 1:1.3, 1:1.4, 1:1.5, 1:1.6, 1:1.7, 1:1.8, 1:1.9, 1:2, 1:2.1, 1:2.2, 1:2.3, 1:2.4, 1:2.5, 1:2.6, 1:2.7, 1:2.8, 1:2.9, or 1:3.

In a further aspect the compositions can comprise from about 1% to about 20% by weight one or more edible oils chosen from olive oil, sunflower oil, sesame oil, coconut oil, canola oil, palm oil, soybean oil, corn oil, safflower oil, peanut oil, or a mixture thereof. In one example, the compositions can comprise olive oil. In another example, from about 1% to about 20% by weight of sesame oil. In a further example, from about 1% to about 20% by weight of coconut oil. In a yet further example, from about 1% to about 20% by weight of soybean oil. In a still further example, from about 1% to about 20% by weight of corn oil.

One aspect of the disclosed compositions relates to compositions comprising:

a) from about 5 mg to about 35 mg of CBD oil wherein the CBD oil contains from about 86% to about 92% by weight of cannabidiol;

b) from about 10 mg to about 70 mg of high oleic acid sunflower oil;

c) from about 30 mg to about 160 mg of sodium bicarbonate;

d) from about 60 mg to about 310 mg of a bile salt extract; and e) from about 90 mg to about 460 mg of one or more carriers.

In one embodiment of this aspect the compositions comprise:

a) from about 5 mg to about 35 mg of CBD oil wherein the CBD oil contains from about 86% to about 92% by weight of cannabidiol;

b) from about 10 mg to about 70 mg of high oleic acid sunflower oil;

c) from about 30 mg to about 160 mg of sodium bicarbonate;

d) from about 60 mg to about 310 mg of a bile salt extract wherein the bile salts are an extract containing from about 45% to about 55% by weight of cholic acid, deoxycholic acid, taurocholate, glycocholic acid, and mixtures thereof; and e) from about 90 mg to about 460 mg of one or more carriers.

In a further embodiment of this aspect the compositions comprise:

a) from about 5 mg to about 35 mg of CBD oil wherein the CBD oil contains from about 86% to about 92% by weight of cannabidiol;

b) from about 10 mg to about 70 mg of high oleic acid sunflower oil;

c) from about 30 mg to about 160 mg of sodium bicarbonate;

d) from about 60 mg to about 310 mg of a bile salt extract; and e) from about 90 mg to about 460 mg of one or more carriers chosen from gum Arabic, tapioca starch, tapioca flour, silicon dioxide, mannitol, colloidal silicon dioxide, and mixture thereof.

In another embodiment of this aspect the compositions comprise:

a) from about 5 mg to about 35 mg of CBD oil wherein the CBD oil contains from about 86% to about 92% by weight of cannabidiol;
b) from about 10 mg to about 70 mg of high oleic acid sunflower oil;
c) from about 30 mg to about 160 mg of sodium bicarbonate;
d) from about 60 mg to about 310 mg of a bile salt extract wherein the bile salts are an extract containing from about 45% to about 55% by weight of cholic acid, deoxycholic acid, taurocholate, glycocholic acid, and mixtures thereof; and
e) from about 90 mg to about 460 mg of one or more carriers chosen from gum Arabic, tapioca starch, tapioca flour, silicon dioxide, mannitol, colloidal silicon dioxide, and mixture thereof.

In a further aspect of the disclosed compositions the compositions comprise:

a) from about 5 mg to about 15 mg of CBD oil wherein the CBD oil contains from about 86% to about 92% by weight of cannabidiol;
b) from about 10 mg to about 30 mg of high oleic acid sunflower oil;
c) from about 30 mg to about 65 mg of sodium bicarbonate;
d) from about 60 mg to about 125 mg of a bile salt extract; and
e) from about 90 mg to about 185 mg of one or more carriers.

In one embodiment of the disclosed compositions comprise:

a) from about 5 mg to about 15 mg of CBD oil wherein the CBD oil contains from about 86% to about 92% by weight of cannabidiol;
b) from about 10 mg to about 30 mg of high oleic acid sunflower oil;
c) from about 30 mg to about 65 mg of sodium bicarbonate;
d) from about 60 mg to about 125 mg of a bile salt extract wherein the bile salts are an extract containing from about 45% to about 55% by weight of cholic acid, deoxycholic acid, taurocholate, glycocholic acid, and mixtures thereof; and
e) from about 90 mg to about 185 mg of one or more carriers.

In one embodiment of the disclosed compositions comprise:

a) from about 5 mg to about 15 mg of CBD oil wherein the CBD oil contains from about 86% to about 92% by weight of cannabidiol;
b) from about 10 mg to about 30 mg of high oleic acid sunflower oil;
c) from about 30 mg to about 65 mg of sodium bicarbonate;
d) from about 60 mg to about 125 mg of a bile salt extract; and
e) from about 90 mg to about 185 mg of one or more carriers chosen from gum Arabic, tapioca starch, tapioca flour, silicon dioxide, mannitol, colloidal silicon dioxide, and mixture thereof.

In one embodiment of the disclosed compositions comprise:

a) from about 5 mg to about 15 mg of CBD oil wherein the CBD oil contains from about 86% to about 92% by weight of cannabidiol;
b) from about 10 mg to about 30 mg of high oleic acid sunflower oil;
c) from about 30 mg to about 65 mg of sodium bicarbonate;
d) from about 60 mg to about 125 mg of a bile salt extract wherein the bile salts are an extract containing from about 45% to about 55% by weight of cholic acid, deoxycholic acid, taurocholate, glycocholic acid, and mixtures thereof; and
e) from about 90 mg to about 185 mg of one or more carriers chosen from gum Arabic, tapioca starch, tapioca flour, silicon dioxide, mannitol, colloidal silicon dioxide, and mixture thereof.

In a further aspect the compositions can comprise from about 10 mg to about 70 mg of one or more edible oils chosen from olive oil, sunflower oil, sesame oil, coconut oil, canola oil, palm oil, soybean oil, corn oil, safflower oil, peanut oil, or a mixture thereof. In one example, the compositions can comprise olive oil. In another example, from about 10 mg to about 70 mg of sesame oil. In a further example, from about 10 mg to about 70 mg of coconut oil. In a yet further example, from about 10 mg to about 70 mg of soybean oil. In a still further example, from about 10 mg to about 70 mg of corn oil.

The disclosed compositions of this aspect are free flowing solids comprising no water or moisture. In general, the compositions are dried by any means necessary before being formed into capsules, pellets, pills, and the like. Depending upon the end use, the formulator may reconstitute the composition in an aqueous carrier. In that case the further addition of an emulsifier, which is typically added by the user, may be necessary.

In one embodiment the one or more carriers are not organic or inorganic acids that can lead to decarboxylation of the sodium bicarbonate, especially if reconstituted by the formulator as an aqueous solution.

The following table provides non-limiting examples of compositions according to this aspect.

TABLE 1

| Ingredients | 1 | 2 | 3 | 4 | 5 |
|---|---|---|---|---|---|
| CBD Oil[1] | 6.07 | 7.59 | 9.11 | 10.62 | 11.58 |
| High oleic acid sunflower oil | 12.15 | 15.18 | 18.22 | 21.26 | 23.17 |
| Sodium bicarbonate | 30.41 | 38.01 | 45.61 | 53.21 | 58 |
| Bile salt extract[2] | 60.29 | 75.36 | 90.43 | 105.50 | 115 |
| Gum Arabic | 91.09 | 113.86 | 136.64 | 159.41 | 173.76 |
| Total | 200 | 250 | 300 | 350 | 381.51 |

[1]Contains from about 86% to about 92% by weight of cannabidiol

[2]Bile salt extract containing from about 45% to about 55% by weight of cholic acid, deoxycholic acid, taurocholate, glycocholic acid, and mixtures thereof.

In a further aspect of the disclosed compositions the compositions comprise:

a) from about 10 mg to about 20 mg of CBD oil wherein the CBD oil contains from about 86% to about 92% by weight of cannabidiol;
b) from about 10 mg to about 30 mg of high oleic acid sunflower oil;
c) from about 55 mg to about 95 mg of sodium bicarbonate;

d) from about 115 mg to about 185 mg of a bile salt extract; and e) from about 180 mg to about 275 mg of one or more carriers.

In one embodiment of the disclosed compositions comprise:

a) from about 10 mg to about 20 mg of CBD oil wherein the CBD oil contains from about 86% to about 92% by weight of cannabidiol;

b) from about 10 mg to about 30 mg of high oleic acid sunflower oil;

c) from about 55 mg to about 95 mg of sodium bicarbonate;

d) from about 115 mg to about 185 mg of a bile salt extract wherein the bile salts are an extract containing from about 45% to about 55% by weight of cholic acid, deoxycholic acid, taurocholate, glycocholic acid, and mixtures thereof; and e) from about 180 mg to about 275 mg of one or more carriers.

In one embodiment of the disclosed compositions comprise:

a) from about 10 mg to about 20 mg of CBD oil wherein the CBD oil contains from about 86% to about 92% by weight of cannabidiol;

b) from about 10 mg to about 30 mg of high oleic acid sunflower oil;

c) from about 55 mg to about 95 mg of sodium bicarbonate;

d) from about 115 mg to about 185 mg of a bile salt extract; and e) from about 180 mg to about 275 mg of one or more carriers chosen from gum Arabic, tapioca starch, tapioca flour, silicon dioxide, mannitol, colloidal silicon dioxide, and mixture thereof.

In one embodiment of the disclosed compositions comprise:

a) from about 10 mg to about 20 mg of CBD oil wherein the CBD oil contains from about 86% to about 92% by weight of cannabidiol;

b) from about 10 mg to about 30 mg of high oleic acid sunflower oil;

c) from about 55 mg to about 95 mg of sodium bicarbonate;

d) from about 115 mg to about 185 mg of a bile salt extract wherein the bile salts are an extract containing from about 45% to about 55% by weight of cholic acid, deoxycholic acid, taurocholate, glycocholic acid, and mixtures thereof; and e) from about 180 mg to about 275 mg mg of one or more carriers chosen from gum Arabic, tapioca starch, tapioca flour, silicon dioxide, mannitol, colloidal silicon dioxide, and mixture thereof.

The following table provides non-limiting examples of compositions according to this aspect.

TABLE 2

| Ingredients | 6 | 7 | 8 | 9 | 10 |
|---|---|---|---|---|---|
| CBD Oil[1] | 12.14 | 13.66 | 15.18 | 16.69 | 17.30 |
| High oleic acid sunflower oil | 24.29 | 27.33 | 30.37 | 33.40 | 46.76 |
| Sodium bicarbonate | 60.81 | 68.41 | 76.01 | 83.62 | 86.66 |
| Bile salt extract[2] | 120.57 | 135.65 | 150.72 | 165.79 | 171.82 |
| Gum Arabic | 182.18 | 204.95 | 227.73 | 250.50 | 259.61 |
| Total | 400 | 450 | 500 | 550 | 582.15 |

[1]Contains from about 86% to about 92% by weight of cannabidiol

[2]Bile salt extract containing from about 45% to about 55% by weight of cholic acid, deoxycholic acid, taurocholate, glycocholic acid, and mixtures thereof.

In a further aspect of the disclosed compositions the compositions comprise:

a) from about 15 mg to about 25 mg of CBD oil wherein the CBD oil contains from about 86% to about 92% by weight of cannabidiol;

b) from about 30 mg to about 50 mg of high oleic acid sunflower oil;

c) from about 90 mg to about 125 mg of sodium bicarbonate;

d) from about 175 mg to about 245 mg of a bile salt extract; and e) from about 270 mg to about 365 mg of one or more carriers.

In one embodiment of the disclosed compositions comprise:

a) from about 15 mg to about 25 mg of CBD oil wherein the CBD oil contains from about 86% to about 92% by weight of cannabidiol;

b) from about 30 mg to about 50 mg of high oleic acid sunflower oil;

c) from about 90 mg to about 125 mg of sodium bicarbonate;

d) from about 175 mg to about 245 mg of a bile salt extract wherein the bile salts are an extract containing from about 45% to about 55% by weight of cholic acid, deoxycholic acid, taurocholate, glycocholic acid, and mixtures thereof; and e) from about 270 mg to about 365 mg of one or more carriers.

In one embodiment of the disclosed compositions comprise:

a) from about 15 mg to about 25 mg of CBD oil wherein the CBD oil contains from about 86% to about 92% by weight of cannabidiol;

b) from about 30 mg to about 50 mg of high oleic acid sunflower oil;

c) from about 90 mg to about 125 mg of sodium bicarbonate;

d) from about 175 mg to about 245 mg of a bile salt extract; and e) from about 270 mg to about 365 mg of one or more carriers chosen from gum Arabic, tapioca starch, tapioca flour, silicon dioxide, mannitol, colloidal silicon dioxide, and mixture thereof.

In one embodiment of the disclosed compositions comprise:

a) from about 15 mg to about 25 mg of CBD oil wherein the CBD oil contains from about 86% to about 92% by weight of cannabidiol;

b) from about 30 mg to about 50 mg of high oleic acid sunflower oil;

c) from about 90 mg to about 125 mg of sodium bicarbonate;

d) from about 175 mg to about 245 mg of a bile salt extract wherein the bile salts are an extract containing from about 45% to about 55% by weight of cholic acid, deoxycholic acid, taurocholate, glycocholic acid, and mixtures thereof; and e) from about 270 mg to about 365 mg of one or more carriers chosen from gum Arabic, tapioca starch, tapioca flour, silicon dioxide, mannitol, colloidal silicon dioxide, and mixture thereof.

The following table provides non-limiting examples of compositions according to this aspect.

TABLE 3

| Ingredients | 11 | 12 | 13 | 14 | 15 |
|---|---|---|---|---|---|
| CBD Oil[1] | 18.21 | 19.73 | 21.25 | 22.76 | 23.37 |
| High oleic acid sunflower oil | 36.44 | 39.48 | 42.51 | 45.55 | 46.76 |
| Sodium bicarbonate | 91.22 | 98.82 | 106.42 | 114.02 | 117.06 |
| Bile salt extract[2] | 180.86 | 195.93 | 211.00 | 226.08 | 232.10 |
| Gum Arabic | 273.27 | 296.04 | 318.82 | 341.59 | 350.70 |
| Total | 600 | 650 | 700 | 750 | 770 |

[1]Contains from about 86% to about 92% by weight of cannabidiol

[2]Bile salt extract containing from about 45% to about 55% by weight of cholic acid, deoxycholic acid, taurocholate, glycocholic acid, and mixtures thereof.

In a yet further aspect the compositions comprise:

a) from about 25 mg to about 35 mg of CBD oil wherein the CBD oil contains from about 86% to about 92% by weight of cannabidiol;

b) from about 50 mg to about 70 mg of high oleic acid sunflower oil;

c) from about 125 mg to about 160 mg of sodium bicarbonate;

d) from about 175 mg to about 310 mg of a bile salt extract; and e) from about 365 mg to about 460 mg of one or more carriers.

In one embodiment of this aspect the compositions comprise:

a) from about 25 mg to about 35 mg of CBD oil wherein the CBD oil contains from about 86% to about 92% by weight of cannabidiol;

b) from about 50 mg to about 70 mg of high oleic acid sunflower oil;

c) from about 125 mg to about 160 mg of sodium bicarbonate;

d) from about 175 mg to about 310 mg of a bile salt extract wherein the bile salts are an extract containing from about 45% to about 55% by weight of cholic acid, deoxycholic acid, taurocholate, glycocholic acid, and mixtures thereof; and e) from about 365 mg to about 460 mg of one or more carriers.

In a further embodiment of this aspect the compositions comprise:

a) from about 5 mg to about 35 mg of CBD oil wherein the CBD oil contains from about 86% to about 92% by weight of cannabidiol;

b) from about 10 mg to about 70 mg of high oleic acid sunflower oil;

c) from about 30 mg to about 160 mg of sodium bicarbonate;

d) from about 175 mg to about 310 mg of a bile salt extract; and e) from about 365 mg to about 460 mg one or more carriers chosen from gum Arabic, tapioca starch, tapioca flour, silicon dioxide, mannitol, colloidal silicon dioxide, and mixture thereof.

In another embodiment of this aspect the compositions comprise:

a) from about 5 mg to about 35 mg of CBD oil wherein the CBD oil contains from about 86% to about 92% by weight of cannabidiol;

b) from about 10 mg to about 70 mg of high oleic acid sunflower oil;

c) from about 30 mg to about 160 mg of sodium bicarbonate;

d) from about 175 mg to about 310 mg of a bile salt extract wherein the bile salts are an extract containing from about 45% to about 55% by weight of cholic acid, deoxycholic acid, taurocholate, glycocholic acid, and mixtures thereof; and e) from about 365 mg to about 460 mg of one or more carriers chosen from gum Arabic, tapioca starch, tapioca flour, silicon dioxide, mannitol, colloidal silicon dioxide, and mixture thereof.

The following table provides non-limiting examples of compositions according to this aspect.

TABLE 4

| Ingredients | 16 | 17 | 18 | 19 | 20 |
|---|---|---|---|---|---|
| CBD Oil[1] | 24.28 | 25.80 | 27.32 | 28.84 | 30.35 |
| High oleic acid sunflower oil | 48.59 | 51.62 | 54.66 | 57.70 | 60.73 |
| Sodium bicarbonate | 121.62 | 129.22 | 136.82 | 144.43 | 152.03 |
| Bile salt extract[2] | 241.15 | 256.22 | 271.29 | 286.36 | 301.43 |
| Gum Arabic | 364.36 | 387.14 | 409.91 | 432.68 | 455.45 |
| Total | 800 | 850 | 900 | 950 | 1000 |

[1]Contains from about 86% to about 92% by weight of cannabidiol

[2]Bile salt extract containing from about 45% to about 55% by weight of cholic acid, deoxycholic acid, taurocholate, glycocholic acid, and mixtures thereof.

Sodium Bicarbonate

The disclosed compositions comprise from about 10% to about 25% by weight of sodium bicarbonate. In one embodiment the compositions comprise from about 12% to about 18% by weight of sodium bicarbonate. In another embodiment the compositions comprise from about 13% to about 17% by weight of sodium bicarbonate. In a further embodiment the compositions comprise from about 14% to about 17% by weight of sodium bicarbonate. The compositions can comprise from about 10% to about 25% by weight of sodium bicarbonate, for example, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5%, 25% by weight of $NaHCO_3$, or any fractional amount thereof.

The disclosed compositions comprise from about 30 mg to about 160 mg of sodium bicarbonate. In one embodiment the compositions comprise from about 30 mg to about 65 mg of sodium bicarbonate. In another embodiment the compositions from about 55 mg to about 95 mg of sodium bicarbonate. In a further embodiment the compositions comprise from about 90 mg to about 125 mg of sodium bicarbonate. In a still further embodiment the compositions comprise from about 125 mg to about 160 mg of sodium bicarbonate.

The disclosed compositions comprise from about 30 mg to about 160 mg of sodium bicarbonate, for example, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, or 160 mg, or any fractional amount thereof.

Bile Salts

The disclosed compositions comprise one or more bile salts as described herein. The source of the bile salts can be any commercially available salts. The disclosed bile salts are typically obtained as a bile salt extract. In some embodiment single bile salts are added, for example, deoxycholic acid.

For the purposes of the present disclosure the terms "bile salts" and "bile acids" are used interchangeably herein. Bile acids are steroid acids found predominantly in the bile of mammals, for example, oxen, goats, and other cattle. The bile salts are conjugated with the amino acids taurine or glycine to produce bile salts. Extracted bile salts can comprise unconjugated bile acids.

Cholic acid, also known as 3α, 7α, 12α-trihydroxy-5β-cholan-24-oic acid is a primary bile acid found in bile extracts. It is insoluble in water (soluble in alcohol and acetic acid), obtained as a white crystalline substance. Salts of cholic acid are referred to as cholates. Cholic acid, along with chenodeoxycholic acid, is one of the two major bile acids produced by the liver of mammals, where it is synthesized from cholesterol. These two major bile acids are roughly equal in concentration in extracts. Bile salts, per se, are made from choloyl-CoA, which exchanges its CoA with either glycine, or taurine, yielding glycocholic and taurocholic acid, respectively. Other bile salts include taurochenodeoxycholic acid and glycochenodeoxycholic acid (derivatives of chenodeoxycholic acid). These together with glycocholic and taurocholic acid make up the major constituents of bile salts.

One non-limiting embodiment of bile salt extracts relates to ox bile salt extracts. One example of ox bile salt extract contains from about 45% to about 55% by weight of an admixture of cholic acid, deoxycholic acid taurocholate and glycocholic acid all of which can be partially or fully conjugated to taurine and glycine. In some embodiments pure acids or acid conjugates are added, for example, deoxycholic acid.

The compositions of the present disclosure comprise from about 25% to about 35% by weight of one or more bile salt extracts. In another embodiment the compositions comprise from about 28% to about 32% by weight of one or more bile salt extracts. In a further embodiment the compositions comprise from about 28% to about 31% by weight of one or more bile salt extracts. In a yet further embodiment the compositions comprise from about 29% to about 32% by weight of one or more bile salt extracts.

The compositions of the present disclosure can comprise from about 25% to about 35% by weight of one or more bile salt extracts, for example, 25% 26%, 27%, 28%, 29%, 30%, 31%, 32%, 33%, 34%, or 35%, or any fractional amount thereof.

The compositions of the present disclosure comprise from about 60 mg to about 310 mg of a bile salt extract. In one embodiment the compositions comprise from about 60 mg to about 125 mg of a bile salt extract. In one embodiment the compositions comprise from about 115 mg to about 185 mg of a bile salt extract. In one embodiment the compositions comprise from about 175 mg to about 245 mg of a bile salt extract. In one embodiment the compositions comprise from about 175 mg to about 310 mg of a bile salt extract.

The compositions can comprise a single bile salt chosen from cholic acid, deoxycholic acid, taurocholate and glycocholic acid. In one embodiment the composition comprises deoxycholic acid.

The compositions of the present disclosure comprise from about 60 mg to about 310 mg of a bile salt extract, for example, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg. 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, or 310 mg, or any fractional amount thereof, for example 141.8 mg, 172.56 mg, or 202.11 mg.

Carriers

The disclosed compositions comprise from about 35% to about 55% by weight of one or more carriers.

In one embodiment the compositions comprise from about 40% to about 50% by weight of one or more carriers. In another embodiment the compositions comprise from about from about 40% to about 50% by weight of one or more carriers. In a further embodiment the compositions comprise from about 35% to about 55% by weight of one or more carriers. In a still further embodiment the compositions comprise from about 42% to about 48% by weight of one or more carriers. In a yet further embodiment the compositions comprise from about 43% to about 47% by weight of one or more carriers. The disclosed compositions can comprise, for example, 35%, 36%, 37%, 38%, 39%, 40%, 41%, 42%, 43%, 44%, 45%, 46%, 47%, 48%, 49%, 50%, 51%, 52%, 53%, 54%, or 55%, by weight of one or more carriers, or any fractional amount thereof.

The disclosed compositions can comprise from about 90 mg to about 460 mg of one or more carriers. In one embodiment, the compositions comprise from about 90 mg to about 185 mg of one or more carriers. In another embodiment, the compositions comprise from about 180 mg to about 275 mg of one or more carriers. In a further embodiment, the compositions comprise from about 270 mg to about 365 mg of one or more carriers. In a still further embodiment, the compositions comprise from about 365 mg to about 460 mg of one or more carriers.

The disclosed compositions can comprise from about 90 mg to about 460 mg of one or more carriers, for example, 90 mg, 91 mg, 92 mg, 93 mg, 94 mg, 95 mg, 96 mg, 97 mg, 98 mg, 99 mg, 100 mg, 101 mg, 102, mg, 103, mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg 31 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 167 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 290 mg, 291 mg, 292 mg, 293 mg, 294 mg, 295 mg, 296 mg, 297 mg, 298 mg, 299 mg, 300 mg, 301 mg, 302 mg, 303 mg, 304 mg, 305 mg, 306 mg, 307 mg, 308 mg, 309 mg, 310 mg, 311 mg, 312 mg, 313 mg, 314 mg, 315 mg, 316 mg, 317 mg, 318 mg, 319 mg, 320 mg, 321 mg, 322 mg, 323 mg, 324 mg, 325 mg, 326 mg, 327 mg, 328 mg, 329 mg, 330 mg, 331 mg, 332 mg, 333 mg, 334 mg, 335 mg, 336 mg, 337 mg, 338 mg, 339 mg, 340 mg, 341 mg, 342 mg, 343 mg, 344 mg, 345 mg, 346 mg, 347 mg, 348 mg, 349 mg, 350 mg, 351 mg, 352 mg, 353 mg, 354 mg, 355 mg, 356 mg, 357 mg, 358 mg, 359 mg, 360 mg, 361 mg, 362 mg, 363 mg, 364 mg, 365 mg, 366 mg, 367 mg, 368 mg, 369 mg, 370 mg, 371 mg, 372 mg, 373 mg, 374 mg, 375 mg, 376 mg, 377 mg, 378 mg, 379 mg, 380 mg, 381 mg, 382 mg, 383 mg, 384 mg, 385 mg, 386 mg, 387 mg, 388 mg, 389 mg, 390 mg, 390 mg, 391 mg, 392 mg, 393 mg, 394 mg, 395 mg, 396 mg, 397 mg, 398 mg, 399 mg, 400 mg, 401 mg, 402 mg, 403 mg, 404 mg, 405 mg, 406 mg, 407 mg, 408 mg, 409 mg, 410 mg, 411 mg, 412 mg, 413 mg, 414 mg, 415 mg, 416 mg, 417 mg, 418 mg, 419 mg, 420 mg, 421 mg, 422 mg, 423 mg, 424 mg, 425 mg, 426 mg, 427 mg, 428 mg, 429 mg, 430 mg, 431 mg, 432 mg, 433 mg, 434 mg, 435 mg, 436 mg, 437 mg, 438 mg, 439 mg, 440 mg, 441 mg, 442 mg, 443 mg, 444 mg, 445 mg, 446 mg, 447 mg, 448 mg, 449 mg, 450 mg, 451 mg, 452 mg, 453 mg, 454 mg, 455 mg, 456 mg, 457 mg, 458 mg, 459 mg, or 460 mg, or any fractional amount thereof.

In one aspect the disclosed carriers are polysaccharides. Non-limiting examples of poly saccharide carriers include inulin, galactogen, cellulose, chitin, pectin, psyllium, guar, hemicellulose, potato starch, and partially hydrolyzed polysaccharides. In another aspect the carriers are sugar alcohols, for example, sorbitol, erythritol, xylitol, lactitol, maltitol, mannitol, hydrogenated starch hydrolysates, isomaltose, or any combination thereof. In a further aspect carrier component is based on a native or chemically modified agar, alginates, carrageenan gum, cellulose, chitosan, chitin, cyclodextrin, dextran, gellan gum, glycogen, glycosaminoglycan, gum karaya, inulin, pectin, polydextrose, xanthan gum, or any other starches, gums or other polysaccharide, including functionalized derivatives, dextrinized, hydrolyzed, oxidized, alkylated, hydroxyalkylated, acetylated, fractionated, and physically modified starches and mixtures thereof. In some embodiments glycerin and/or propylene glycol can be added as a carrier.

In another aspect the carrier is chosen from gum Arabic, tapioca starch, tapioca flour, silicon dioxide, mannitol, colloidal silicon dioxide, and mixture thereof. In a further example the carrier is gum Arabic. In another example the carrier is inulin. In a yet another example the carrier is microcrystalline cellulose. In a still further example, the carrier is D-lactose monohydrate. In a still another example the carrier is quillaia. The carrier can be a combination of gum Arabic, inulin, microcrystalline cellulose, D-lactose monohydrate, or quillaia.

In one non-limiting example the carrier is mannitol, a non-limiting example is Partek™ mannitol, available from Partek Inc. In a further non-limiting example, the carrier is microcrystalline cellulose. In a still further example, the carrier is colloidal silicon dioxide. In a still further example, the carrier is colloidal silicon dioxide. One non-limiting example is Aeroperl® 300 available from IMCD. In a further embodiment the one or more carriers chosen from gum Arabic, tapioca starch, tapioca flour, silicon dioxide, mannitol, colloidal silicon dioxide, and mixture thereof. In one non-limiting example, the carrier is gum Arabic.

Methods

Disclosed herein are methods for treating diabetes in a subjected suffering from diabetes. The disclosed method comprises administering to a subject in need of treatment a composition comprising:

a) from about 0.5% to about 10% by weight of CBD oil wherein the CBD oil contains from about 86% to about 92% by weight of cannabidiol;
b) from about 1% to about 20% by weight of high oleic acid sunflower oil;
c) from about 10% to about 25% by weight of sodium bicarbonate;
d) from about 25% to about 35% by weight of one or more bile salt extracts; and
e) from about 35% to about 55% by weight of one or more carriers.

In another aspect the disclosed methods comprise administering to a subject in need of treatment a composition comprising:

a) from about 5 mg to about 35 mg of CBD oil wherein the CBD oil contains from about 86% to about 92% by weight of cannabidiol;
b) from about 10 mg to about 70 mg of high oleic acid sunflower oil;
c) from about 30 mg to about 160 mg of sodium bicarbonate;

d) from about 60 mg to about 310 mg of a bile salt extract; and e) from about 90 mg to about 460 mg of one or more carriers.

As it relates to the treatment of diabetes, any of the disclosed compositions can be used as an effective means for treating diabetes. The disclosed methods are also effective for reducing body weight (see FIG. 7 and FIG. 8) and improving triglyceride and glucose levels in patients in need of treatment.

In one embodiment the composition comprises from about 5 mg to about 15 mg of CBD oil wherein the CBD oil contains from about 86% to about 92% by weight of cannabidiol. In another embodiment the composition comprises from about 10 mg to about 20 mg of CBD oil wherein the CBD oil contains from about 86% to about 92% by weight of cannabidiol. In a further embodiment the composition comprises from about 15 mg to about 25 mg of CBD oil wherein the CBD oil contains from about 86% to about 92% by weight of cannabidiol. In a yet further embodiment the composition comprises from about 25 mg to about 35 mg of CBD oil wherein the CBD oil contains from about 86% to about 92% by weight of cannabidiol.

In one embodiment the composition comprises from about 10 mg to about 30 mg of high oleic acid sunflower oil. In another embodiment the composition comprises from about 30 mg to about 50 mg of high oleic acid sunflower oil. In a further embodiment the composition comprises from about 50 mg to about 70 mg of high oleic acid sunflower oil.

In one embodiment the composition comprises from about 30 mg to about 160 mg of sodium bicarbonate. In another embodiment the composition comprises from about 30 mg to about 65 mg of sodium bicarbonate. In a further embodiment the composition comprises from about 55 mg to about 95 mg of sodium bicarbonate. In a yet further embodiment the composition comprises from about 90 mg to about 125 mg of sodium bicarbonate.

In one embodiment the composition comprises from about 60 mg to about 125 mg of a bile salt extract wherein the bile salt extract contains from about 45% to about 55% by weight of cholic acid, deoxycholic acid, taurocholate, glycocholic acid, and mixtures thereof. In another embodiment the composition comprises from about 115 mg to about 185 mg of a bile salt extract wherein the bile salt extract contains from about 45% to about 55% by weight of cholic acid, deoxycholic acid, taurocholate, glycocholic acid, and mixtures thereof. In a further embodiment the composition comprises from about 175 mg to about 245 mg of a bile salt extract wherein the bile salt extract contains from about 45% to about 55% by weight of cholic acid, deoxycholic acid, taurocholate, glycocholic acid, and mixtures thereof.

In one embodiment the one or more carriers are chosen from gum Arabic, tapioca starch, tapioca flour, silicon dioxide, mannitol, colloidal silicon dioxide, and mixture thereof.

In one embodiment the carrier is gum Arabic.

The disclosed methods deliver from about 15 mg/kg of cannabidiol to a subject being treated for diabetes. As disclosed herein above, specific embodiments of the disclosed composition comprise from about 200 mg to about 1000 mg of the composition per dose. As such, the disclosed compositions can be used to deliver from about 15 mg/kg to about 400 mg/kg of cannabidiol to a subject being treated. For example, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg. 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 91 mg/kg, 92 mg/kg, 93 mg/kg, 94 mg/kg, 95 mg/kg, 96 mg/kg, 97 mg/kg, 98 mg/kg, 99 mg/kg, 100 mg/kg, 101 mg/kg, 102, mg/kg, 103, mg/kg, 104 mg/kg, 105 mg/kg, 106 mg/kg, 107 mg/kg, 108 mg/kg, 109 mg/kg, 110 mg/kg, 111 mg/kg, 112 mg/kg, 113 mg/kg, 114 mg/kg, 115 mg/kg, 116 mg/kg, 117 mg/kg, 118 mg/kg, 119 mg/kg, 120 mg/kg, 121 mg/kg, 122 mg/kg, 123 mg/kg, 124 mg/kg, 125 mg/kg, 126 mg/kg, 127 mg/kg, 128 mg/kg, 129 mg/kg, 130 mg 31 mg/kg, 132 mg/kg, 133 mg/kg, 134 mg/kg, 135 mg/kg, 136 mg/kg, 137 mg/kg, 138 mg/kg, 139 mg/kg, 140 mg/kg, 141 mg/kg, 142 mg/kg, 143 mg/kg, 144 mg/kg, 145 mg/kg, 146 mg/kg, 147 mg/kg, 148 mg/kg, 149 mg/kg, 150 mg/kg, 151 mg/kg, 152 mg/kg, 153 mg/kg, 154 mg/kg, 155 mg/kg, 156 mg/kg, 157 mg/kg, 158 mg/kg, 159 mg/kg, 160 mg/kg, 161 mg/kg, 162 mg/kg, 163 mg/kg, 164 mg/kg, 165 mg/kg, 166 mg/kg, 167 mg/kg, 168 mg/kg, 169 mg/kg, 170 mg/kg, 171 mg/kg, 172 mg/kg, 173 mg/kg, 174 mg/kg, 175 mg/kg, 167 mg/kg, 177 mg/kg, 178 mg/kg, 179 mg/kg, 180 mg/kg, 181 mg/kg, 182 mg/kg, 183 mg/kg, 184 mg/kg, 185 mg/kg, 186 mg/kg, 187 mg/kg, 188 mg/kg, 189 mg/kg, 190 mg/kg, 191 mg/kg, 192 mg/kg, 193 mg/kg, 194 mg/kg, 195 mg/kg, 196 mg/kg, 197 mg/kg, 198 mg/kg, 199 mg/kg, 200 mg/kg, 201 mg/kg, 202 mg/kg, 203 mg/kg, 204 mg/kg, 205 mg/kg, 206 mg/kg, 207 mg/kg, 208 mg/kg, 209 mg/kg, 210 mg/kg, 211 mg/kg, 212 mg/kg, 213 mg/kg, 214 mg/kg, 215 mg/kg, 216 mg/kg, 217 mg/kg, 218 mg/kg, 219 mg/kg, 220 mg/kg, 221 mg/kg, 222 mg/kg, 223 mg/kg, 224 mg/kg, 225 mg/kg, 226 mg/kg, 227 mg/kg, 228 mg/kg, 229 mg/kg, 230 mg/kg, 231 mg/kg, 232 mg/kg, 233 mg/kg, 234 mg/kg, 235 mg/kg, 236 mg/kg, 237 mg/kg, 238 mg/kg, 239 mg/kg, 240 mg/kg, 241 mg/kg, 242 mg/kg, 243 mg/kg, 244 mg/kg, 245 mg/kg, 246 mg/kg, 247 mg/kg, 248 mg/kg, 249 mg/kg, 250 mg/kg, 251 mg/kg, 252 mg/kg, 253 mg/kg, 254 mg/kg, 255 mg/kg, 256 mg/kg, 257 mg/kg, 258 mg/kg, 259 mg/kg, 260 mg/kg, 261 mg/kg, 262 mg/kg, 263 mg/kg, 264 mg/kg, 265 mg/kg, 266 mg/kg, 267 mg/kg, 268 mg/kg, 269 mg/kg, 270 mg/kg, 271 mg/kg, 272 mg/kg, 273 mg/kg, 274 mg/kg, 275 mg/kg, 276 mg/kg, 277 mg/kg, 278 mg/kg, 279 mg/kg, 280 mg/kg, 281 mg/kg, 282 mg/kg, 283 mg/kg, 284 mg/kg, 285 mg/kg, 286 mg/kg, 287 mg/kg, 288 mg/kg, 289 mg/kg, 290 mg/kg, 290 mg/kg, 291 mg/kg, 292 mg/kg, 293 mg/kg, 294 mg/kg, 295 mg/kg, 296 mg/kg, 297 mg/kg, 298 mg/kg, 299 mg/kg, 300 mg/kg, 301 mg/kg, 302 mg/kg, 303 mg/kg, 304 mg/kg, 305 mg/kg, 306 mg/kg, 307 mg/kg, 308 mg/kg, 309 mg/kg, 310 mg/kg, 311 mg/kg, 312 mg/kg, 313 mg/kg, 314 mg/kg, 315 mg/kg, 316 mg/kg, 317 mg/kg, 318 mg/kg, 319 mg/kg, 320 mg/kg, 321 mg/kg, 322 mg/kg, 323 mg/kg, 324 mg/kg, 325 mg/kg, 326 mg/kg, 327 mg/kg, 328 mg/kg, 329 mg/kg, 330 mg/kg, 331 mg/kg, 332 mg/kg, 333 mg/kg, 334 mg/kg, 335 mg/kg, 336 mg/kg, 337 mg/kg, 338 mg/kg, 339 mg/kg, 340 mg/kg, 341 mg/kg, 342 mg/kg, 343 mg/kg, 344 mg/kg, 345 mg/kg, 346 mg/kg, 347 mg/kg, 348 mg/kg, 349 mg/kg, 350 mg/kg, 351 mg/kg, 352 mg/kg, 353 mg/kg, 354 mg/kg, 355 mg/kg, 356 mg/kg, 357 mg/kg, 358 mg/kg, 359 mg/kg, 360 mg/kg, 361 mg/kg, 362 mg/kg, 363 mg/kg, 364 mg/kg, 365 mg/kg, 366 mg/kg, 367 mg/kg, 368 mg/kg, 369 mg/kg, 370 mg/kg, 371 mg/kg, 372 mg/kg, 373 mg/kg, 374 mg/kg, 375 mg/kg, 376 mg/kg, 377 mg/kg, 378 mg/kg, 379 mg/kg, 380 mg/kg, 381 mg/kg, 382 mg/kg, 383 mg/kg, 384 mg/kg, 385 mg/kg, 386 mg/kg, 387 mg/kg, 388 mg/kg, 389 mg/kg, 390 mg/kg, 390 mg/kg, 391 mg/kg, 392 mg/kg, 393 mg/kg, 394 mg/kg, 395 mg/kg, 396 mg/kg, 397 mg/kg, 398 mg/kg, 399 mg/kg, or 400 mg/kg of cannabidiol.

The disclosed method relates to administering a sufficient amount of the composition such that from about 30 mg/kg to about 100 mg/kg of cannabidiol is administered to the subject. In another embodiment the disclosed method relates to administering a sufficient amount of the composition such that from about 30 mg/kg to about 50 mg/kg of cannabidiol is administered to the subject. In a further embodiment the disclosed method relates to administering a sufficient amount of the composition such that from about 15 mg/kg to about 35 mg/kg of cannabidiol is administered to the subject. In a yet further embodiment the disclosed method relates to administering a sufficient amount of the composition such that from about 10 mg/kg to about 30 mg/kg of cannabidiol is administered to the subject.

Any of the disclosed compositions, active ingredients, carriers, or processing aids can be administered together in any amount prescribed by a medical authority to treat diabetes.

Animal Study

Test Animals

Zucker diabetic rats were used in the following study. The Zucker diabetic fatty (ZDF) Rat (Obese fa/fa; CRL strain code 370) was derived from a spontaneous mutation to the leptin receptor gene that arose in a colony of outbred Zucker rats held in the Eli Lilly Research Laboratories in Indianapolis, IN. These animals have been widely used in rodent model studies in order to explore the clinical conditions relating to obesity and type 2 diabetes in humans. This phenotype can be used to study overt obesity, hyperphagia, hypercholesterolaemia, hyperlipoidaemia and hyperglycemia. The ZDF Rat (Lean fa/+; CRL strain code 380) is the control model for the ZDF Rat in this study. In contrast to the homozygous ZDF (fa/fa) obese rat, the ZDF lean rat only carries one copy of the mutated leptin receptor gene.

The objective of the present study was to examine the effect of the disclosed compositions on body weight, blood glucose, cholesterol, and lipid content in the ZDF rat. The disclosed compositions were administered at two dose levels based on acute tolerability. The initial treatment period was one month, but due to positive observations made over this period, two separate treatment extensions were conducted. The treatment phase was preceded by a validation phase to first confirm the obese and diabetic phenotype of the ZDF rat relative to the Lean fa/+ control.

Study Design

Twenty-four (24) male Zucker Diabetic Fatty obese rats (ZDF fa/fa, CRL strain code 370) and eight (8) male Zucker Diabetic Fatty lean rats (ZDF fa/+, CRL strain code 380), at 3 months of age from Charles River Laboratories entered the study. The Zucker obese rats are homozygous for fatty genes (fa/fa) while the Zucker lean rats carry only one recessive fatty gene (fa/+). Animals arrived in the facility and acclimatized to the new environment prior to testing. Subjects were kept on a 12 hour/12 hour light/dark cycle with all experimental activities taking place during the animals' light cycle. Animals were fed Purina LabDiet® 5008 ad libitum. Water was also provided ad libitum to all study subjects.

ZDF fa/fa animals were allocated based on equivalent body weight and blood glucose measures prior to the testing phase. The treatment phase began for 28 days with daily dosing respective to treatment group, daily body weights and bi-weekly blood collections. Treatment phase extension 1 added another 28 days of daily dosing, body weight data collection and bi-weekly blood collection. There was no break between Treatment phase and Treatment phase extension 1. Locomotor activity, food consumption and water consumption data were also collected. After completion of Treatment phase extension 1, there was a washout period of 43 days. Treatment phase extension 2 was initiated after the washout period and involved 14 days of daily treatment of either vehicle or DEHYDRATECH™ CBD 30 mg/kg. Body weights were collected daily and blood collection occurred at the end of the study to perform blood chemistry and examine inflammatory biomarkers.

Study Schedule

Table 5 Provides a summary of each experimental phase and the procedures accompanying each phase.

TABLE 5

| Phase | Procedures |
|---|---|
| Validation | Daily body weight/observation |
| Treatment | Blood collection days 1, 13 and 27. Animals allocated into groups based on body weight and blood results from day 27 |
| Treatment Extension - 1 | Daily composition administered from Table Y at 30 mg/kg and 100 mg/kg. Blood collected days 35, 42, and 56 |
| Washout | 6 Weeks no procedures |
| Treatment Extension - 2 | Daily composition administered from Table Y at 30 mg/kg for 14 days. Daily body weights. |
| Final blood Collection | Blood collect after final administration |

Test Protocol

1. Validation Phase

Blood Collection and Analysis

Blood was collected (0.8 ml) on study days 0, 13, and 27 via the saphenous vein (SOP ROD.14) into CAT serum separator tubes with clot activator. Blood glucose was measured upon first puncture with the Accu-Chek® glucose meter. Blood samples were collected in the morning and left undisturbed for 15 minutes at 4° C. to allow the blood to clot. Samples were centrifuged at 4,500 RCF for 5 minutes at 4° C. to obtain serum and serum samples were sent to Antech Diagnostics to measure total cholesterol and triglyceride levels.

Group Allocation

ZDF obese rats were allocated into 1 of 3 treatment groups on Day 28 by balancing body weight and blood results from Day 27 of the validation phase. ZDF lean animals were allocated to Group A as a non-diabetes control group.

2. Treatment Phase

Treatment phase began on Day 29 with animals administered with either Vehicle, composition 1 CBD 30 mg/kg containing (CBD30), or composition 2 containing CBD 100 mg/kg (CBD100).

Test Article

Table 6 describes the tested compositions. Composition 1 delivered 30 mg/kg of CD oil containing 90.64% cannabidiol. Composition 2 delivered 100 mg/kg of CD oil containing 90.64% cannabidiol. Upon arrival, test articles were stored at approximately 4° C. with desiccant and protected from light for the duration of the study.

TABLE 6

| Ingredients (mg) | 1 | 2 | Effective % |
|---|---|---|---|
| CBD Oil[1] | 34.74 | 115.8 | 3.04[1] |
| High oleic acid sunflower oil | 69.51 | 231.7 | 6.07 |
| Sodium bicarbonate | 174 | 580 | 15.2 |
| Ox bile extract | 345 | 1150 | 30.14 |
| Gum Arabic | 521.28 | 1737.6 | 45.55 |
| Total | 1144.53 | 3815.1 | 100 |

[1]CBD oil contains 90.64% cannabidiol for an effective dose of 2.6%.

Blood Collection

Blood was collected (0.8 mL) on study Days 35, 42, 56 (i.e day 7, 14, 28 post treatment) via saphenous vein (SOP ROD. 14) into 0.8 mL CAT serum separator tubes with clot activator. Blood glucose was immediately measured at first puncture via Accu-Chek® glucose meter. Blood samples were left undisturbed for 15 minutes at 4° C. to clot. Samples were centrifuged (4,500 RCF for 5 minutes at 4° C.) to obtain serum. Samples were then sent to Antech Diagnostics to measure cholesterol and triglyceride levels.

Health Observation and Body Weights

Daily observations were performed according to SOP ROD.19. Body weights were recorded daily as per SOP ROD.08.

3. Treatment Extension Phase 1

The treatment phase was extended without cessation of treatment administration for 28 days. All 32 subjects continued to receive their assigned daily oral treatment as described in Section I.3. Blood collections occurred on days 70 and 84. At the end of this phase, a 60-minute locomotor activity assessment was collected, and 24-hour food and water consumption were recorded.

Washout Period

During the washout period, animals did not receive any treatment. Health observations were completed daily.

4. Treatment Extension Phase 2

Study extension for 21 subjects (8 ZDF lean, 13 ZDF obese) for an additional 14 days.

Test Article Administration

For 14 days, vehicle and compositions 1 and 2 from Table 6 were prepared and administered as described above.

Blood Collection

Blood collection was performed after the additional 14 days of test article administration in 21 study animals (13 ZDF obese and 8 ZDF lean), approximately 0.85 mL of whole blood was collected via saphenous vein according to facility SOP. Whole blood was divided equally into two separate aliquots. The collected aliquots were shipped to Antech Diagnostics for Complete Blood Cell Count (CBC) and clinical chemistry profile.

Cholesterol

During the treatment phase, differences in total cholesterol levels were identified. Repeated measures ANOVA recorded a main effect of group ($F_{(3,28)}$=48.06; p<0.0001) and day ($F_{(4,112)}$=97.157; p<0.0001). Dunnett's post hoc testing attributed these differences to higher cholesterol levels in ZDF obese animal groups compared to the ZDF lean (obese vehicle, obese CBD30, obese CBD100 all p<0.0001 vs lean). Dunnett testing against the obese vehicle group identified significantly higher cholesterol levels in the obese CBD100 compared to the obese vehicle group (p=0.01). Repeated measures ANOVA restricted to the ZDF obese groups recorded a significant effect on treatment ($F_{(2,21)}$=3.95; p=0.03). Dunnett post hoc testing found higher levels of cholesterol in the composition 2 group compared to ZDF obese vehicle animals.

Based on these results, the types of cholesterol (HDL and LDL) were further investigated by IDEXX. After analysis of the HDL-LDL cholesterol composition, HDL cholesterol was noted to be significantly higher in obese animal groups compared to lean controls ($F_{(3,27)}$=38.77; p<0.0001, Tukey's post hoc testing lean vs each obese group p<0.0001). Furthermore, LDL cholesterol was found to be significantly higher in the composition 2 group compared to all other groups ($F_{(3,27)}$=21.81; p<0.0001, Tukey's post hoc testing of the composition 2 group vs all other group p<0.0001). Therefore, the increase in total cholesterol seen in the composition 2 dose group suggests this measure was largely contributed by increased levels of LDL cholesterol.

Table 7 to Table 10 provide the cholesterol levels (mmol/L) of each group of animals from the start of the experiment through day 84.

TABLE 7

| | | Cholesterol (mmol/L) | | | | | | | |
|---|---|---|---|---|---|---|---|---|---|
| Group | Animal | Day 0 | Day 13 | Day 27 | Day 35 | Day 42 | Day 56 | Day 70 | Day 84 |
| ZDF | A1 | 2.8 | 2.9 | 2.5 | 2.9 | 3 | 2.8 | 3.1 | 2.9 |
| Lean | A2 | 2.5 | 2.9 | 2.5 | 2.7 | 2.4 | 3.3 | 3.2 | 2.9 |
| Vehicle | A3 | 2.7 | 3.1 | 2.8 | 2.8 | 2.7 | 3 | 3.3 | 2.9 |
| | A4 | 2.7 | 2.9 | 2.4 | 2.7 | 2.7 | 2.8 | 3.2 | 2.9 |
| | A5 | 2.6 | 2.9 | 2.4 | 2.5 | 2.9 | 3 | 3.7 | 2.8 |
| | A6 | 2.8 | 3.1 | 2.7 | 2.6 | 3.1 | 3 | 2.9 | 2.9 |
| | A7 | 2.4 | 2.6 | 2.5 | 2.4 | 2.7 | 3.2 | 2.9 | 2.8 |
| | A8 | 2.5 | 2.8 | 2.5 | 2.6 | 2.6 | 3 | 2.8 | 2.7 |
| | Average | 2.63 | 2.90 | 2.54 | 2.65 | 2.76 | 3.01 | 3.14 | 2.85 |
| | SEM | 0.05 | 0.06 | 0.05 | 0.06 | 0.08 | 0.06 | 0.10 | 0.03 |

TABLE 8

| | | Cholesterol (mmol/L) | | | | | | | |
|---|---|---|---|---|---|---|---|---|---|
| ZDF | B1 | 4 | 3.9 | 4.8 | 4.7 | 4.8 | 6 | 6.5 | 6.2 |
| Obese | B2 | 4.3 | 5.3 | 5.5 | 6 | 5.9 | 6.2 | 7.4 | 6.2 |
| Vehicle | B3 | 4 | 5 | 4.9 | 4.8 | 5.2 | 5.6 | 6.5 | 6.9 |
| | B4 | 3.9 | 4.8 | 6.8 | 6.6 | 7.7 | 9.5 | 12.5 | 12 |
| | B5 | 4.4 | 4.9 | 5.9 | 6.2 | 5.9 | 7 | 7.5 | 7.1 |
| | B6 | 3.4 | 3.4 | 3.7 | 3.8 | 4.3 | 5.2 | 6 | 6.2 |
| | B7 | 4.7 | 6.9 | 6.5 | 6.1 | 6.4 | 7 | 8.4 | 9.4 |
| | B8 | 3.5 | 4.9 | 5.4 | 5 | 5.3 | 6.9 | 5. | 6.2 |
| | Average | 4.03 | 4.89 | 5.44 | 5.40 | 5.69 | 6.68 | 7.56 | 7.53 |
| | SEM | 0.16 | 0.36 | 0.35 | 0.34 | 0.37 | 0.47 | 0.77 | 0.75 |

TABLE 9

| Cholesterol (mmol/L) | | | | | | | | | |
|---|---|---|---|---|---|---|---|---|---|
| Comp. | C1 | 3.7 | 3.9 | 4 | 4.8 | 5 | 5.9 | 6.4 | 6.2 |
| CBD | C2 | 4 | 4.3 | 4.7 | 5.5 | 5.9 | 7.4 | 7.9 | 8 |
| 30 | C3 | 4 | 4.5 | 5.3 | 5.9 | 5.7 | 6.7 | 7.7 | 8 |
| mg/kg | C4 | 3.7 | 5.2 | 5.5 | 5.5 | 5.6 | 6.7 | 6.7 | 7 |
| | C5 | 3.9 | 4.6 | 5.8 | 6.1 | 6 | 7.7 | 8.8 | 8.5 |
| | C6 | 3.6 | 4.8 | 5.5 | 5.9 | 6.8 | 7.4 | 8.6 | 10.1 |
| | C7 | 4.2 | 5.2 | 5.7 | 6.1 | 5.9 | 7.9 | 8.8 | 10 |
| | C8 | 3.8 | 5 | 4.9 | 5.2 | 5. | 6.7 | 7.7 | 7.9 |
| Average | | 3.86 | 4.699 | 5.18 | 5.63 | 5.83 | 7.05 | 7.83 | 8.21 |
| SEM | | 0.07 | 0.16 | 0.21 | 0.16 | 0.18 | 0.23 | 0.32 | 0.47 |

TABLE 10

| Cholesterol (mmol/L) | | | | | | | | | |
|---|---|---|---|---|---|---|---|---|---|
| Comp. | D1 | 3.6 | 4.6 | 4.9 | 6.3 | 7 | 8.5 | 10.6 | 9.9 |
| CBD | D2 | 3.5 | 3.7 | 4 | 6.2 | 6.1 | 6.9 | 7.5 | 9.2 |
| 100 | D3 | 4.2 | 5.6 | 6.2 | 6.8 | 7.3 | 8.7 | 11.3 | 13 |
| mg/kg | D4 | 3.7 | 4.5 | 5.1 | 5.3 | 5.1 | 7.2 | 8 | 8.5 |
| | D5 | 3.9 | 5.4 | 5.5 | 7 | 7.1 | 8.5 | 9.2 | 9.6 |
| | D6 | 4.3 | 5.3 | 5.6 | 6.3 | 6.9 | 7.3 | 8.6 | 9.5 |
| | D7 | 4.8 | 4.7 | 55 | 5.8 | 6.2 | 8.4 | 10.1 | 10.5 |
| | D8 | 3.5 | 4.8 | 5.3 | 5.2 | 6.1 | 8.1 | 9.1 | 10.1 |
| Average | | 3.94 | 4.83 | 5.26 | 6.11 | 6.48 | 7.95 | 9.30 | 10.04 |
| SEM | | 0.16 | 0.22 | 0.23 | 0.23 | 0.26 | 0.2 | 0.46 | 0.47 |

Figure 2:
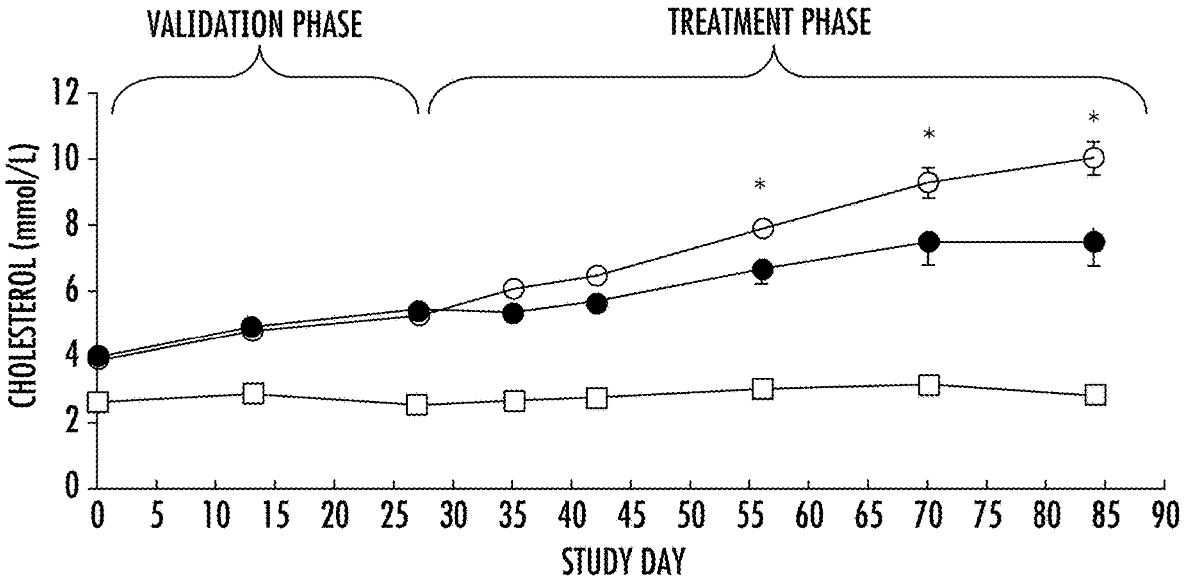
FIG. 2 shows the cholesterol levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated.

FIG. 1 and FIG. 2 summarize the results of the cholesterol testing. FIG. 1 shows the cholesterol levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated. The 30 mg/kg dosage tracks well with the ZDFD obese vehicle treated animals.

FIG. 2 shows the cholesterol levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated. The 100 mg/kg dosage is higher than the ZDFD obese vehicle treated animals.

Triglycerides

Triglycerides were analyzed and found to be significantly different between groups ($F_{(3.28)}=29.46$; $p<0.0001$) and to be significantly affected by day ($F_{(4.112)}=13.75$; $p<0.0001$). Dunnett post hoc testing against Lean animals found significantly higher triglyceride levels in all ZDF obese groups compared to ZDF lean animals ($p<0.0001$ all comparisons). Dunnett testing against obese vehicle animals found a significant difference between lean ($p<0.0001$) and obese CBD30 treated animals ($p=0.01$). To better detect differences of treatment in ZDF obese animals, triglycerides were analyzed without the lean group. Repeated ANOVA found a significant effect of group ($F_{(2.21)}=3.95$; $p=0.04$). Dunnett post hoc testing found significantly lower triglyceride levels in the obese CBD30 group compared to obese vehicle ($p=0.02$). Dunnett testing did not find a significant difference between obese vehicle and obese CBD100 ($p=0.15$).

Table 11 to Table 14 provide the cholesterol levels (mmol/L) of each group of animals from the start of the experiment through day 84.

TABLE 11

| Triglycerides (mmol/L) | | | | | | | | | |
|---|---|---|---|---|---|---|---|---|---|
| Group | Animal | Day 0 | Day 13 | Day 27 | Day 35 | Day 42 | Day 56 | Day 70 | Day 84 |
| ZDF | A1 | 1.73 | 2.69 | 2.18 | 1.74 | 1.89 | 1.95 | 2.61 | 2.51 |
| Lean | A2 | 0.74 | 1.39 | 1.1 | 1.25 | 1.71 | 1.99 | 2.01 | 2.39 |
| Vehicle | A3 | 1.74 | 2.01 | 1.87 | 1.75 | 1.67 | 2.68 | 3.08 | 3.51 |
| | A4 | 1.67 | 1.91 | 1.48 | 3.21 | 2.32 | 2.92 | 1.72 | 2.49 |
| | A5 | 1.54 | 1.58 | 1.54 | 1.69 | 1.66 | 3.38 | 2.39 | 2.46 |
| | A6 | 1.14 | 1.47 | 2.05 | 1.28 | 1.82 | 3.04 | 1.3 | 1.96 |
| | A7 | 1.8 | 2.23 | 1.37 | 1.36 | 1.9 | 2.46 | 1.75 | 3.11 |
| | A8 | 2.27 | 1.98 | 1.68 | 2.3 | 1.98 | 2.64 | 2.15 | 2.79 |
| | Average | 1.58 | 1.92 | 1.66 | 1.82 | 1.86 | 2.63 | 2.13 | 2.65 |
| | SEM | 0.16 | 0.16 | 0.13 | 0.23 | 0.08 | 0.148 | 0.2. | 0.17 |

TABLE 12

| Triglycerides (mmol/L) | | | | | | | | | |
|---|---|---|---|---|---|---|---|---|---|
| ZDF | B1 | 11.25 | 13.57 | 18.65 | 21.64 | 19.42 | 20.69 | 22.37 | 17.19 |
| Obese | B2 | 7.82 | 8.36 | 4.35 | 7.74 | 8.92 | 9.85 | 11.96 | 11.14 |
| Vehicle | B3 | 14.23 | 11.11 | 9.17 | 10.09 | 9.86 | 12.59 | 12.71 | 16.23 |
| | B4 | 12.97 | 18.89 | 17.35 | 17.52 | 21.79 | 20.16 | 21.39 | 34.57 |
| | B5 | 13.92 | 11.48 | 8.39 | 8.36 | 11.12 | 9.95 | 14.43 | 14.88 |
| | B6 | 9.16 | 10.61 | 11.97 | 14.7 | 13.51 | 12.83 | 10.15 | 12.81 |
| | B7 | 11.49 | 10.82 | 10.53 | 11.67 | 11.19 | 13.58 | 19.59 | 21.02 |
| | B8 | 12.2 | 21.58 | 18.51 | 13.94 | 14.9 | 10.2 | 13.11 | 12.42 |
| Average | | 11.63 | 13.30 | 12.37 | 13.21 | 13.84 | 13.73 | 15.71 | 17.53 |
| SEM | | 0.79 | 1.61 | 1.87 | 1.68 | 1.64 | 1.55 | 1.66 | 2.67 |

TABLE 13

| Triglycerides (mmol/L) | | | | | | | | | |
|---|---|---|---|---|---|---|---|---|---|
| Comp. | C1 | 10.23 | 13.21 | 13.87 | 4.09 | 11.44 | 14.05 | 14.38 | 11.77 |
| CBD | C2 | 12.4 | 10.83 | 8.6 | 9.04 | 9.93 | 9.51 | 12.49 | 12.49 |
| 30 | C3 | 10.9 | 15.2 | 15.41 | 4.42 | 10.5 | 11.5 | 12.39 | 16.1 |
| mg/kg | C4 | 12.33 | 10.6 | 10.93 | 9.58 | 8.85 | 9.82 | 8.67 | 12.4 |
| | C5 | 14.91 | 15.66 | 11.13 | 9.62 | 11.44 | 14.71 | 13.68 | 7.9 |
| | C6 | 10.46 | 14.48 | 8.11 | 8.01 | 8.89 | 11.45 | 11.83 | 15.43 |
| | C7 | 9.8 | 11.18 | 6.72 | 8.48 | 7.1 | 9.2 | 9.71 | 17.57 |
| | C8 | 5.65 | 4.53 | 5.87 | 4.57 | 5.65 | 7.83 | 8.09 | 8.31 |
| Average | | 10.84 | 11.96 | 10.08 | 7.23 | 9.23 | 11.01 | 11.41 | 12.75 |
| SEM | | 0.94 | 1.28 | 1.19 | 0.86 | 0.73 | 0.85 | 0.82 | 1.24 |

TABLE 14

| Triglycerides (mmol/L) | | | | | | | | | |
|---|---|---|---|---|---|---|---|---|---|
| Comp. | D1 | 10.8 | 17.1 | 15.56 | 15.56 | 12.46 | 14.93 | 15.25 | 15.83 |
| CBD | D2 | 12.98 | 15.84 | 18.24 | 14.2 | 14.89 | 16.33 | 13.39 | 17.57 |
| 100 | D3 | 15.5 | 16.5 | 15.39 | 12.9 | 11.68 | 14.05 | 17.12 | 20.46 |
| mg/kg | D4 | 9.39 | 10.48 | 10.2 | 10.45 | 7.89 | 10.29 | 13.52 | 17.96 |
| | D5 | 15.06 | 13.68 | 10.69 | 11.69 | 7.44 | 8.41 | 9.08 | 10.27 |
| | D6 | 10.86 | 7.81 | 6.48 | 11.28 | 7.5 | 8.11 | 8.8 | 10.28 |
| | D7 | 9.44 | 12.38 | 5.008 | 6.14 | 6.76 | 11.37 | 13.57 | 16.71 |
| | D8 | 9.63 | 15.6 | 12.35 | 7.58 | 7.52 | 8.38 | 8.32 | 9.08 |
| Average | | 11.71 | 13.71 | 11.75 | 11.23 | 9.52 | 11.48 | 12.38 | 14.80 |
| SEM | | 0.88 | 1.16 | 1.61 | 1.12 | 1.08 | 1.15 | 1.15 | 1.50 |

Figure 3:
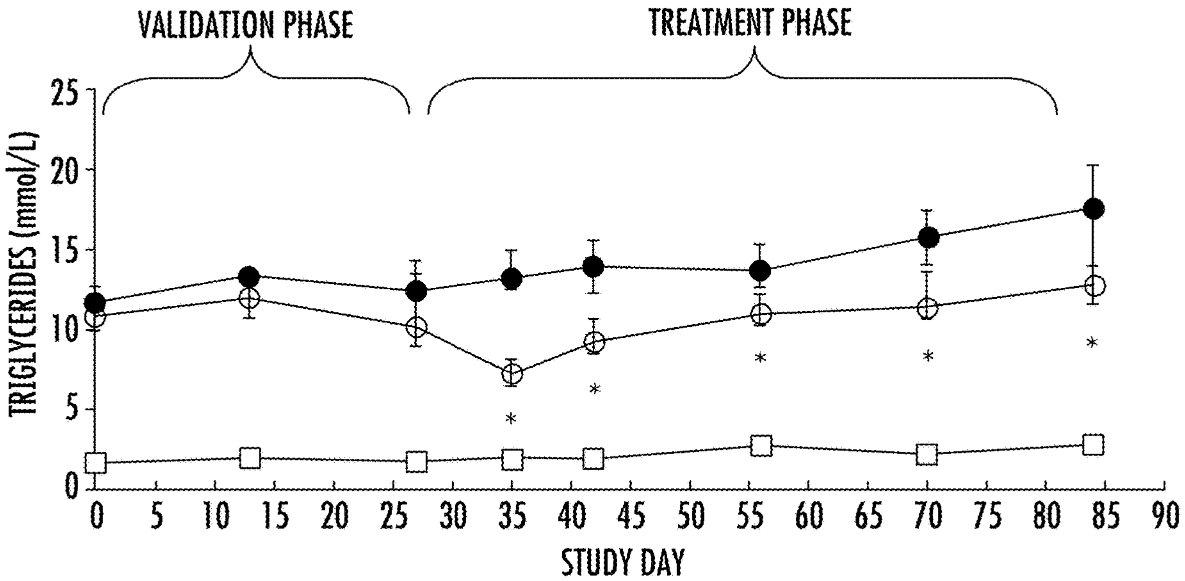
FIG. 3 shows the triglyceride levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated.

FIG. 3 shows the triglyceride levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated. The animals given the 30 mg/kg dosage of CBD had the lowest triglyceride levels with respect to the ZDFD obese vehicle treated animals. The triglyceride levels of the 30 mg/kg animals were significantly reduced as compared to control as indicated by the asterisk, *.

Figure 4:
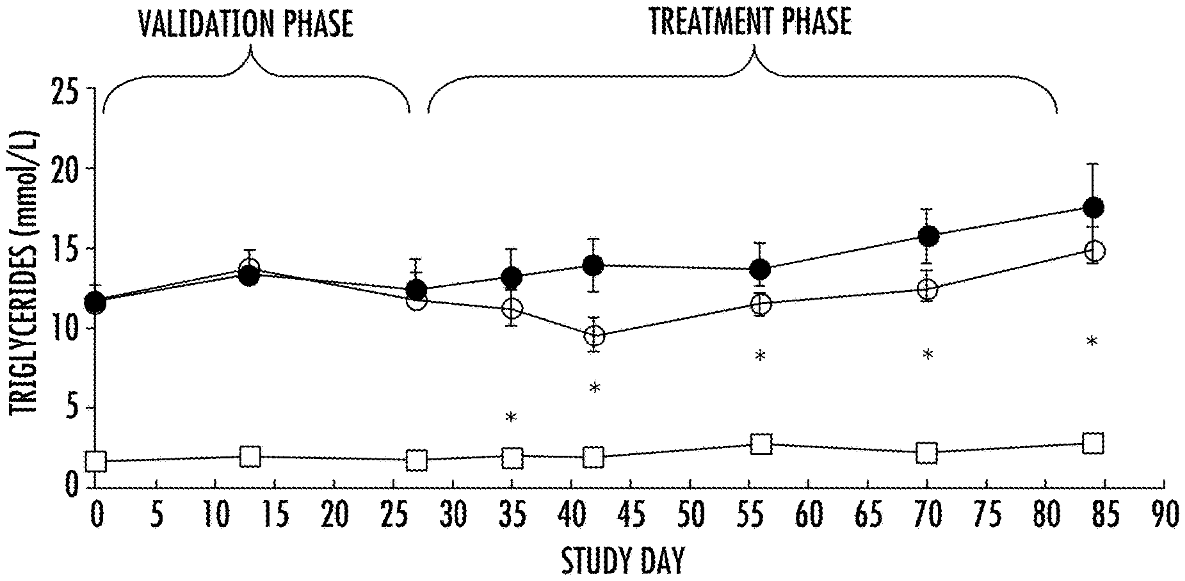
FIG. 4 shows the triglyceride levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated.

FIG. 4 shows the triglyceride levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated. The animals given the 100 mg/kg dosage of CBD had the lower triglyceride levels with respect to the ZDFD obese vehicle treated animals. The triglyceride levels of the 100 mg/kg animals were significantly reduced as compared to control as indicated by the asterisk, *.

Blood Glucose

Blood glucose measured throughout the study found a significant main effect of group ($F_{(3.28)}$=37.68; $p<0.0001$) and day ($F_{(4.112)}$=4.83; $p=0.001$). Post hoc testing with a Dunnett test comparing obese groups to lean animals found significantly lower blood glucose levels in lean animals compared to all ZDF obese groups (obese vehicle $p<0.0001$, obese CBD30 $p<0.0001$, obese CBD100 $p<0.0001$). No differences were detected between obese vehicle and obese CBD30 or CBD100 following Dunnett post hoc testing. Post hoc testing for changes over time (days) found glucose levels increased over time. Repeated measures ANOVA completed without the lean group used to detect subtle changes between the ZDF obese vehicle and ZDF CBD treated groups. No significant effect of treatment ($F_{(2.21)}$ =0.09; $p=0.91$) was recorded but an effect of day was still present with glucose levels increasing overtime ($F_{(4.84)}$ =4.57; $p=0.002$).

Table 15 to Table 18 show the blood glucose levels of the ZDF Lean vehicle control animals, ZDF obese vehicle control animals, animals dosed with a disclosed composition described in Table 6 wherein the composition is dosed such that 30 mg/kg of CBD is given, and animals dosed with a disclosed composition described in Table 6 wherein the composition is dosed such that 100 mg/kg of CBD is given,

TABLE 15

| Blood Glucose (mmol/L) | | | | | | | | | |
|---|---|---|---|---|---|---|---|---|---|
| Group | Animal | Day 0 | Day 13 | Day 27 | Day 35 | Day 42 | Day 56 | Day 70 | Day 84 |
| ZDF | A1 | 5.9 | 5.3 | 5.9 | 6.3 | 5.1 | 5.5 | 6 | 6 |
| Lean | A2 | 6.7 | 5.9 | 7.4 | 5.5 | 5.2 | 6.8 | 6 | 5 |
| Vehicle | A3 | 5.9 | 7.1 | 3.4 | 5.7 | 5.4 | 6.3 | 6 | 5.7 |
| | A4 | 6.6 | 6.1 | 4.9 | 6.6 | 5.3 | 6.4 | 5.8 | 5.9 |
| | A5 | 6.3 | 6.2 | 6 | 6.1 | 5.7 | 5.7 | 5.9 | 5.9 |
| | A6 | 6.4 | 6.3 | 5.6 | 5.4 | 5.2 | 6.1 | 6.4 | 6 |
| | A7 | 6.7 | 6.2 | 6 | 5.3 | 5.7 | 5.7 | 6 | 5.4 |
| | A8 | 5.8 | 6.2 | 5.7 | 5.3 | 5.8 | 6 | 5.2 | 6.4 |
| Average | | 6.29 | 6.16 | 5.61 | 5.78 | 5.43 | 6.06 | 5.91 | 5.79 |
| SEM | | 0.13 | 0.18 | 0.40 | 0.18 | 0.10 | 0.15 | 0.12 | 0.15 |

TABLE 16

| Blood Glucose (mmol/L) | | | | | | | | | |
|---|---|---|---|---|---|---|---|---|---|
| Group | Animal | Day 0 | Day 13 | Day 27 | Day 35 | Day 42 | Day 56 | Day 70 | Day 84 |
| ZDF | B1 | 6.9 | 6.9 | 9.4 | 9.2 | 14.8 | 19.1 | 19.1 | 23.9 |
| Obese | B2 | 24.3 | 30.4 | 24.3 | 27.6 | 27.1 | 26.8 | 26.4 | 29.2 |
| Vehicle | B3 | 21.2 | 28.9 | 26.5 | 26.4 | 26.4 | 25 | 27.1 | 28.6 |
| | B4 | 8.5 | 25.5 | 25.1 | 22.4 | 24.3 | 24.5 | 24.7 | 25 |
| | B5 | 18.7 | 22.7 | 25.7 | 29.1 | 24 | 27.2 | 23.8 | 27.8 |
| | B6 | 8.2 | 7.7 | 13.5 | 22.4 | 23.3 | 23.8 | 24.8 | 24.8 |
| | B7 | 23.5 | 27.5 | 28.1 | 27 | 29.2 | 26.5 | 26.5 | 31.2 |
| | B8 | 6.9 | 13.4 | 24 | 24.2 | 24 | 24 | 24.8 | 28.9 |
| | Average | 14.78 | 20.38 | 22.08 | 23.50 | 24.14 | 24.61 | 24.65 | 27.43 |
| | SEM | 2.77 | 3.4 | 2.39 | 2.21 | 1.51 | 0.91 | 0.89 | 0.91 |

TABLE 17

| Blood Glucose (mmol/L) | | | | | | | | | |
|---|---|---|---|---|---|---|---|---|---|
| Group | Animal | Day 0 | Day 13 | Day 27 | Day 35 | Day 42 | Day 56 | Day 70 | Day 84 |
| Discl. | C1 | 6.4 | 7.2 | 10 | 7.2 | 7.8 | 10.5 | 18.6 | 21.3 |
| Comp. | C2 | 20 | 25.1 | 26.5 | 31.1 | 28.9 | 27.8 | 18.7 | 29.1 |
| CBD | C3 | 10.2 | 15.4 | 23.3 | 22.1 | 23.9 | 27.6 | 25.6 | 31.3 |
| 30 | C4 | 14.7 | 22.6 | 22.3 | 26.7 | 27.6 | 28.6 | 28 | 28.2 |
| mg/kg | C5 | 13.7 | 22.5 | 25.6 | 28.3 | 27.5 | 29 | 24.7 | 25.1 |
| | C6 | 17.3 | 24.4 | 24 | 27.1 | 25.4 | 29.4 | 25.5 | 26.5 |
| | C7 | 21.5 | 24.8 | 24.8 | 26.5 | 29.6 | 29.1 | 25.2 | 27.5 |
| | C8 | 23.6 | 28.1 | 28.2 | 29.1 | 30.1 | 33 | 29.2 | 29.2 |
| | Average | 15.93 | 21.28 | 23.09 | 24.76 | 25.10 | 26.88 | 25.69 | 27.28 |
| | SEM | 2.06 | 2.39 | 1.98 | 2.67 | 2.58 | 2.41 | 1.18 | 1.08 |

TABLE 18

| Blood Glucose (mmol/L) | | | | | | | | | |
|---|---|---|---|---|---|---|---|---|---|
| Group | Animal | Day 0 | Day 13 | Day 27 | Day 35 | Day 42 | Day 56 | Day 70 | Day 84 |
| Discl. | D1 | 9 | 18.9 | 23.3 | 25.7 | 24.1 | 27.9 | 27.6 | 26.7 |
| Comp. | D2 | 6.5 | 8 | 13.5 | 8.7 | 9.5 | 11 | 7.7 | 11.1 |
| CBD | D3 | 19 | 25.6 | 28.5 | 28.9 | 28.2 | 30.5 | 26.9 | 28.8 |
| 100 | D4 | 23.9 | 25.6 | 25.9 | 29.9 | 28.9 | 29.4 | 27.7 | 28.5 |
| mg/kg | D5 | 20.6 | 21.1 | 25.2 | 27.2 | 25.6 | 28.7 | 27.5 | 26.7 |
| | D6 | 22.2 | 22.2 | 23.3 | 27 | 28.7 | 27.4 | 28.3 | 27.5 |
| | D7 | 21.5 | 28.2 | 24.5 | 25.2 | 29 | 29.2 | 27.5 | 25.3 |
| | D8 | 8.4 | 19.5 | 23.3 | 23.7 | 25.5 | 26.9 | 26 | 27.2 |
| | Average | 16.39 | 21.14 | 23.44 | 24.54 | 24.94 | 26.38 | 24.90 | 25.23 |
| | SEM | 2.53 | 2.20 | 1.55 | 2.37 | 2.30 | 2.23 | 2.47 | 2.05 |

Figure 5:
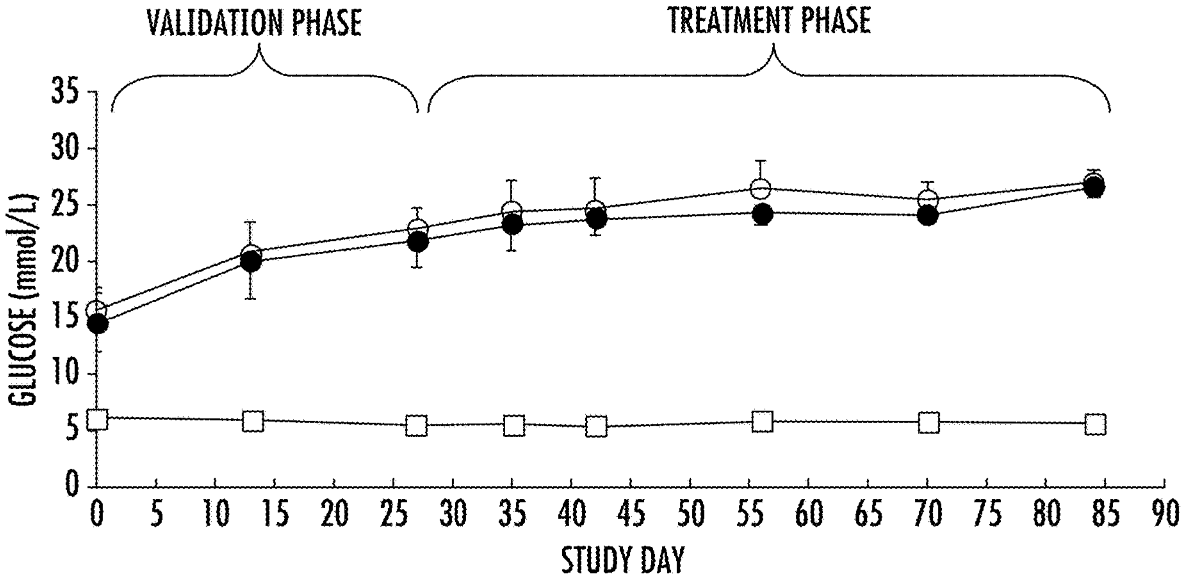
FIG. 5 shows the blood glucose levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated.

FIG. 5 shows the blood glucose levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The validation phase and treatment phase are indicated. The animals given the 30 mg/kg dosage of CBD showed little or no difference in glucose levels compared to the ZDFD obese vehicle treated animals.

Figure 6:
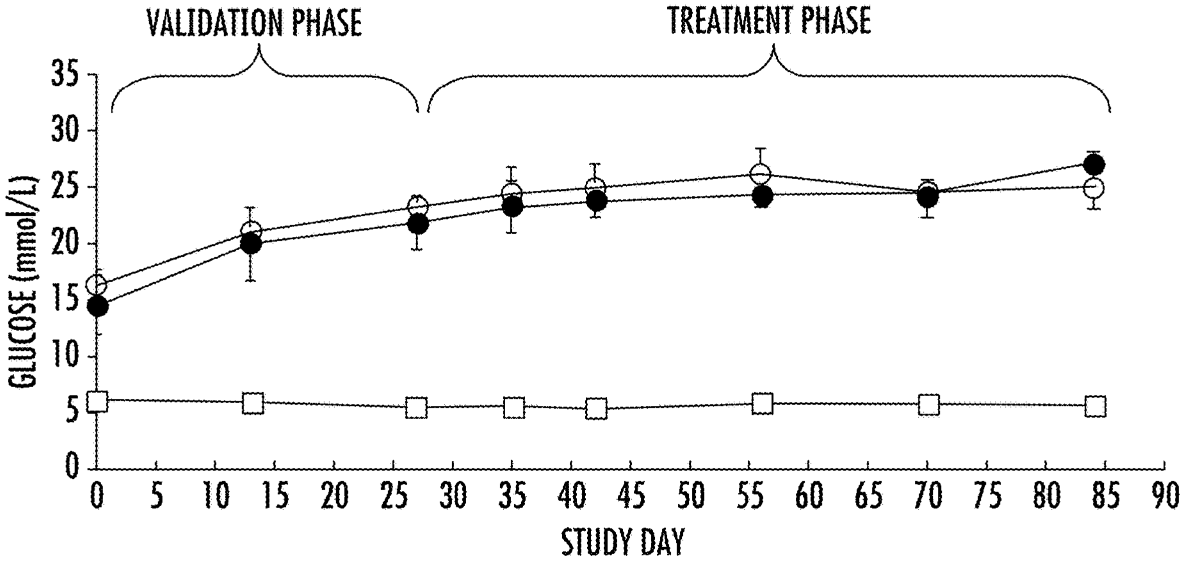
FIG. 6 shows the blood glucose levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated.

FIG. 6 shows the blood glucose levels during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The validation phase and treatment phase are indicated. The animals given the 100 mg/kg dosage of CBD showed little or no difference in glucose levels compared to the ZDFD obese vehicle treated animals.

Figure 7:
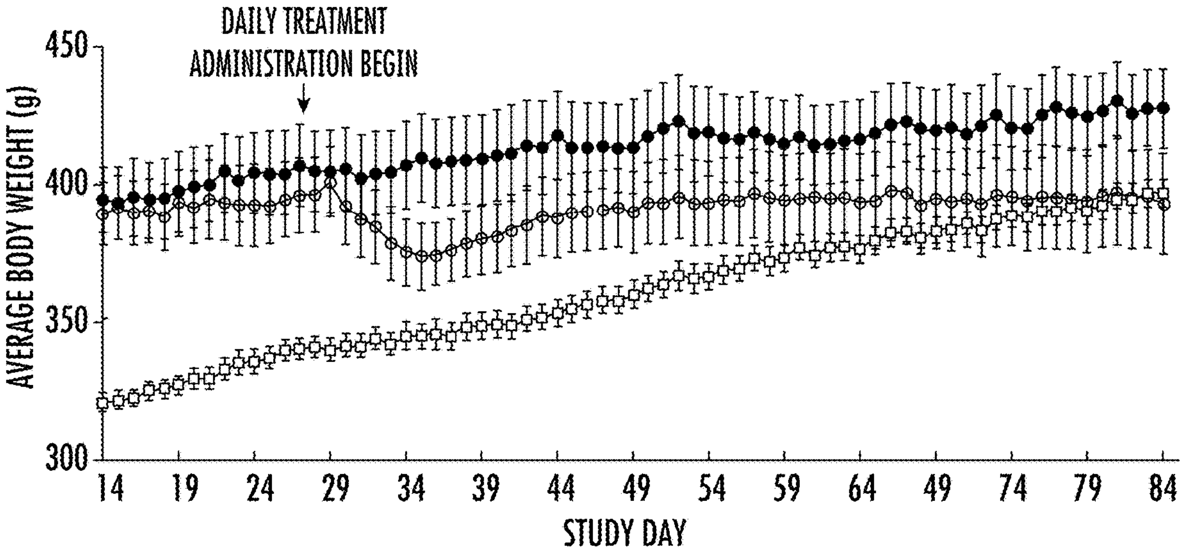
FIG. 7 shows the body weight during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The treatment phase is indicated.

FIG. 7 shows the body weight during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 30 mg/kg cannabidiol. The treatment phase is indicated.

Figure 8:
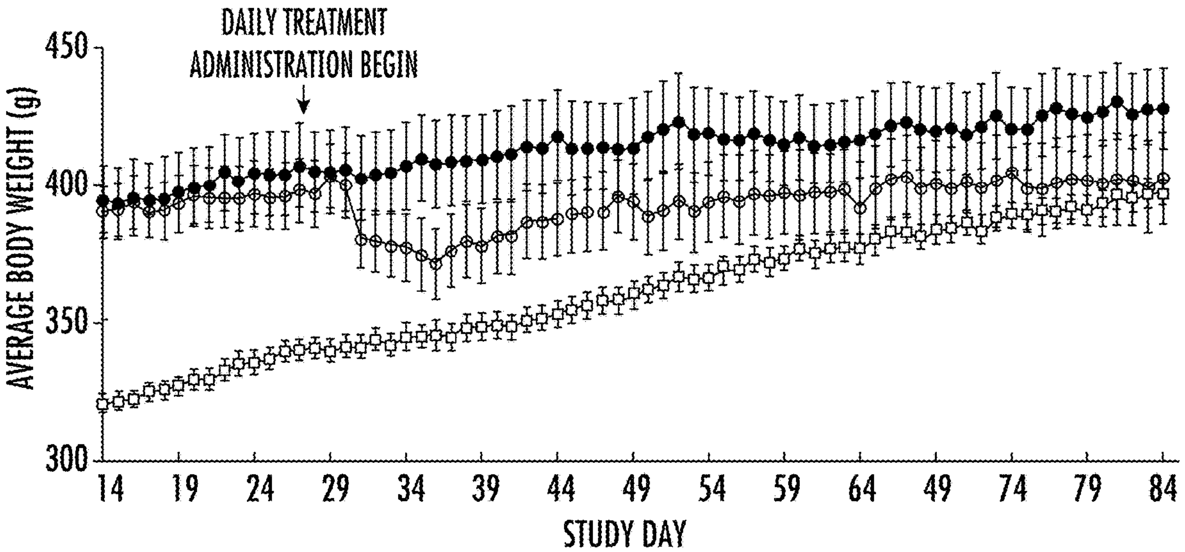
FIG. 8 shows the body weight during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The treatment phase is indicated.

FIG. 8 shows the body weight during study days 0 to 85 for the following animals: ZDF fa/+ (lean) rats (□) given vehicle only, ZDF fa/fa (obese) rats (●) given vehicle only, and ZDF fa/fa (obese) rats (○) given a disclosed composition providing 100 mg/kg cannabidiol. The treatment phase is indicated.

As depicted in FIG. 7 and FIG. 8, beginning just four days after the start of dosing with the disclosed compositions providing 30 mg/kg (■) and 100 g/kg (♦) of cannabidiol, the obese rats (●) began to lose weight. The weight loss was maximized nine days after dosing and maintained throughout the 8-week study duration. This demonstrates an approximately 7% loss of body weight throughout the course of treatment at both cannabidiol levels. Only the treated animal weighed less at the end of the study than at the beginning, whereas the weight of the untreated obese animals trended upwards throughout the study. The lean untreated animals gained the most weight of all and became obese by the end of the study.

Figure 9:
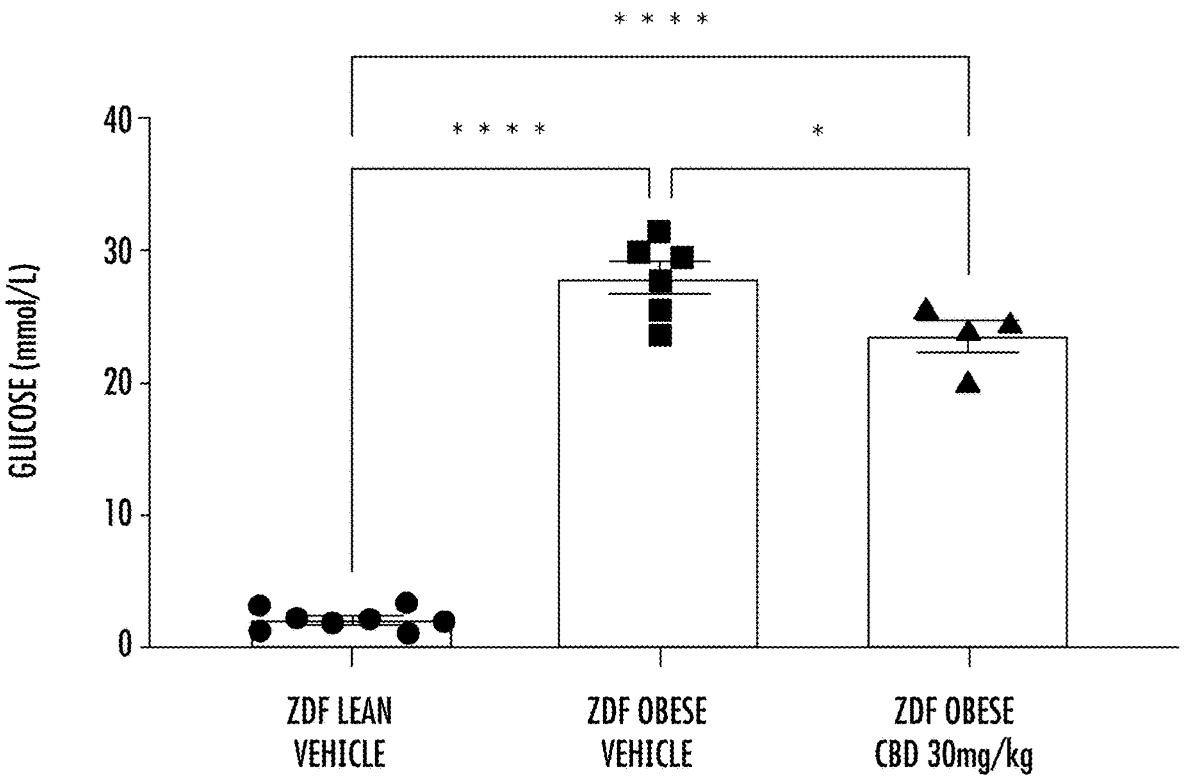
FIG. 9 compares the change in the glucose level of lean animals (control) (●), obese animals (control) (■), and obese animals treated with 30 mg/kg of cannabidiol (▲).

FIG. 9 compares the change in the glucose level of lean animals (control) (●), obese animals (control) (■), and obese animals treated with 30 mg/kg of cannabidiol (▲). The symbol * indicates statistically significant difference in glucose (mmol/L).

Other advantages which are obvious and which are inherent to the disclosure will be evident to one skilled in the art. It will be understood that certain features and sub-combinations are of utility and may be employed without reference to other features and sub-combinations. This is contemplated by and is within the scope of the claims. Since many possible embodiments can be made relating to this disclosure without departing from the scope thereof, it is to be understood that all matter herein set forth or shown in the accompanying drawings is to be interpreted as illustrative and not in a limiting sense.

What is claimed is:

1. A method for treating diabetes comprising administering to a subject in need of treatment a composition comprising:
- a) from about 5 mg to about 35 mg of CBD oil wherein the CBD oil contains from about 86% to about 92% by weight of cannabidiol;
- b) from about 10 mg to about 70 mg of high oleic acid sunflower oil;
- c) from about 30 mg to about 160 mg of sodium bicarbonate;
- d) from about 60 mg to about 310 mg of a bile salt extract; and
- e) from about 90 mg to about 460 mg of one or more carriers.

2. The method according to claim 1, wherein the composition comprises from about 5 mg to about 15 mg of CBD oil wherein the CBD oil contains from about 86% to about 92% by weight of cannabidiol.

3. The method according to claim 1, wherein the composition comprises from about 10 mg to about 20 mg of CBD oil wherein the CBD oil contains from about 86% to about 92% by weight of cannabidiol.

4. The method according to claim 1, wherein the composition comprises from about 15 mg to about 25 mg of CBD oil wherein the CBD oil contains from about 86% to about 92% by weight of cannabidiol.

5. The method according to claim 1, wherein the composition comprises from about 25 mg to about 35 mg of CBD oil wherein the CBD oil contains from about 86% to about 92% by weight of cannabidiol.

6. The method according to claim 1, wherein the composition comprises from about 10 mg to about 30 mg of high oleic acid sunflower oil.

7. The method according to claim 1, wherein the composition comprises from about 30 mg to about 50 mg of high oleic acid sunflower oil.

8. The method according to claim 1, wherein the composition comprises from about 50 mg to about 70 mg of high oleic acid sunflower oil.

9. The method according to claim 1, wherein the composition comprises from about 30 mg to about 160 mg of sodium bicarbonate.

10. The method according to claim 1, wherein the composition comprises from about 30 mg to about 65 mg of sodium bicarbonate.

11. The method according to claim 1, wherein the composition comprises from about 55 mg to about 95 mg of sodium bicarbonate.

12. The method according to claim 1, wherein the composition comprises from about 90 mg to about 125 mg of sodium bicarbonate.

13. The method according to claim 1, wherein the composition comprises from about 60 mg to about 125 mg of a bile salt extract wherein the bile salt extract contains from about 45% to about 55% by weight of cholic acid, deoxycholic acid, taurocholate, glycocholic acid, and mixtures thereof.

14. The method according to claim 1, wherein the composition comprises from about 115 mg to about 185 mg of a bile salt extract wherein the bile salt extract contains from about 45% to about 55% by weight of cholic acid, deoxycholic acid, taurocholate, glycocholic acid, and mixtures thereof.

15. The method according to claim 1, wherein the composition comprises from about 175 mg to about 245 mg of a bile salt extract wherein the bile salt extract contains from about 45% to about 55% by weight of cholic acid, deoxycholic acid, taurocholate, glycocholic acid, and mixtures thereof.

16. The method according to claim 1, wherein the one or more carriers are chosen from gum Arabic, tapioca starch, tapioca flour, silicon dioxide, mannitol, colloidal silicon dioxide, and mixture thereof.

17. The method according to claim 1, wherein the carrier is gum Arabic.

18. A method for treating diabetes comprising administering to a subject in need of treatment a composition comprising:
- a) from about 5 mg to about 35 mg of CBD oil wherein the CBD oil contains from about 86% to about 92% by weight of cannabidiol;
- b) from about 10 mg to about 70 mg of high oleic acid sunflower oil;
- c) from about 30 mg to about 160 mg of sodium bicarbonate;
- d) from about 60 mg to about 310 mg of a bile salt extract; and
- e) from about 90 mg to about 460 mg of one or more carriers;

wherein the composition is in the form of a tablet, pill, or capsule, each tablet, pill or capsule containing from about 200 mg to about 1000 mg of the composition.

19. The method according to claim 18, wherein the subject is administered from about 15 mg/kg to about 400 mg/kg of the composition.

20. The method according to claim 18, wherein the subject is administered a sufficient amount of the composition such that from about 30 mg/kg to about 100 mg/kg of cannabidiol is administered to the subject.

21. The method according to claim 18, wherein the subject is administered a sufficient amount of the composition such that from about 30 mg/kg to about 50 mg/kg of cannabidiol is administered to the subject.

22. The method according to claim 18, wherein the subject is administered a sufficient amount of the composition such that from about 15 mg/kg to about 35 mg/kg of cannabidiol is administered to the subject.

23. The method according to claim 18, wherein the subject is administered a sufficient amount of the composition such that from about 10 mg/kg to about 30 mg/kg of cannabidiol is administered to the subject.

24. A method for treating diabetes comprising administering to a subject in need of treatment a composition comprising:

a) from about 0.5% to about 10% by weight of CBD oil wherein the CBD oil contains from about 86% to about 92% by weight of cannabidiol;

b) from about 1% to about 20% by weight of high oleic acid sunflower oil;

c) from about 10% to about 25% by weight of sodium bicarbonate;

d) from about 25% to about 35% by weight of one or more bile salt extracts; and e) from about 35% to about 55% by weight of one or more carriers.

25. The method according to claim 24, wherein the composition comprises from about 1% to about 4% by weight of CBD oil wherein the CBD oil contains from about 86% to about 92% by weight of cannabidiol.

26. The method according to claim 24, wherein the composition comprises from about 2% to about 4% by weight of CBD oil wherein the CBD oil contains from about 86% to about 92% by weight of cannabidiol.

27. The method according to claim 24, wherein the composition comprises from about 2.5% to about 4% by weight of CBD oil wherein the CBD oil contains from about 86% to about 92% by weight of cannabidiol.

28. The method according to claim 24, wherein the composition comprises about 3% by weight of CBD oil wherein the CBD oil contains from about 86% to about 92% by weight of cannabidiol.

29. A method for treating diabetes comprising administering to a subject in need of treatment a composition comprising:

a) from about 0.5% to about 10% by weight of CBD oil wherein the CBD oil contains from about 86% to about 92% by weight of cannabidiol;

b) from about 1% to about 20% by weight of high oleic acid sunflower oil;

c) from about 10% to about 25% by weight of sodium bicarbonate;

d) from about 25% to about 35% by weight of one or more bile salt extracts; and e) from about 35% to about 55% by weight of one or more carriers;

wherein the amount of cannabidiol administered to the subject is from about 15 mg/kg to about 400 mg/kg of cannabidiol.

30. The method according to claim 29, wherein the composition comprises:

a) about 3% by weight of CBD oil wherein the CBD oil contains from about 89% to about 91% by weight of cannabidiol;

b) about 6% by weight of high oleic acid sunflower oil;

c) about 15% by weight of sodium bicarbonate;

d) about 30% by weight of one or more bile salt extracts; and e) from about 45% to about 55% by weight of one or more carriers.

* * * * *